US012778899B2

(12) United States Patent
Behl et al.

(10) Patent No.: US 12,778,899 B2
(45) **Date of Patent: *Nov. 3, 2026**

(54) OCULAR DRUG DELIVERY

(71) Applicant: Waterford Institute of Technology, Waterford (IE)

(72) Inventors: Gautam Behl, Waterford (IE); Sangeeta Kumari, Waterford (IE); Niall O'Reilly, Waterford (IE); Orla O'Donovan, Waterford (IE); Peter Mcloughlin, Waterford (IE); David Kent, Waterford (IE); Laurence Fitzhenry, Waterford (IE); Elke Behaeghel, Waterford (IE)

(73) Assignee: Waterford Institute of Technology, Waterford (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/458,828

(22) Filed: Aug. 30, 2023

(65) Prior Publication Data

US 2024/0207195 A1 Jun. 27, 2024

Related U.S. Application Data

(63) Continuation of application No. 16/955,336, filed as application No. PCT/IB2018/060528 on Dec. 21, 2018, now Pat. No. 11,779,543.

(30) Foreign Application Priority Data

Dec. 22, 2017 (GB) ...................................... 1721832

(51) Int. Cl.

| | |
|---|---|
| ***A61K 9/51*** | (2006.01) |
| ***A61F 9/00*** | (2006.01) |
| ***A61K 9/00*** | (2006.01) |
| ***A61K 31/573*** | (2006.01) |
| *A61K 45/06* | (2006.01) |
| *B82Y 5/00* | (2011.01) |

(52) U.S. Cl.

CPC .......... *A61K 9/5123* (2013.01); *A61F 9/0026* (2013.01); *A61K 9/0048* (2013.01); *A61K 31/573* (2013.01); *A61K 45/06* (2013.01); *B82Y 5/00* (2013.01)

(58) Field of Classification Search

CPC .. A61K 9/5123; A61K 9/0026; A61K 9/0048; A61K 31/573; A61K 45/06; A61F 9/0026; B82Y 5/00

See application file for complete search history.

(56) References Cited

U.S. PATENT DOCUMENTS

| | | | | |
|---|---|---|---|---|
| 11,779,543 | B2 * | 10/2023 | Behl | A61K 31/56 424/498 |
| 2009/0238865 | A1 | 9/2009 | Heurtault et al. | |
| 2010/0233275 | A1 | 9/2010 | Saulnier et al. | |
| 2010/0266676 | A1 | 10/2010 | Saulnier et al. | |
| 2012/0148669 | A1 | 6/2012 | Benoit et al. | |
| 2013/0273123 | A1 | 10/2013 | Blume | |
| 2021/0085603 | A1 | 3/2021 | Behl et al. | |
| 2021/0085618 | A1 | 3/2021 | Behl et al. | |

FOREIGN PATENT DOCUMENTS

| | | | | |
|---|---|---|---|---|
| EP | 1531800 B1 | | 6/2011 | |
| WO | WO-2011116963 A2 | * | 9/2011 | A61K 8/9794 |
| WO | WO2015142853 A1 | | 9/2015 | |

OTHER PUBLICATIONS

European Office Action dated Jun. 7, 2023 in European Application No. 18839625.3, a corresponding foreign application of U.S. Appl. No. 16/955,336, 5 pages.

Gonzalez-Mira et al, "Optimizing Flurbiprofen-loaded NLC by Central Composite Factorial Design for Ocular Delivery," Nanotechnology, Dec. 2010, 22(4):45101, 15 pages.

Hathout, et al., "Liposomes as an Ocular Delivery System for the Acetazloamide: In Vitro and In Vivo Studies", 8 AAPS PharmSciTech E1, E4-E6, 2007, 12 pages.

PCT Search Report and Written Opinion dated Jun. 27, 2019 in PCT Application No. PCT/IB2018/060528, 11 pages.

Lalu, et al., "Novel nanosystems for the treatment of ocular inflammation: Current paradigms and future research directions", 268 J Control., Rel. 19, 2017, 21 pages.

Sánchez-López et al., "Lipid nanoparticles (SLN, NLC): Overcoming the anatomical and physiological barriers of the eye—Part II—Ocular drug-loaded lipid nanoparticles," Oct. 2016, European Journal of Pharmaceutics and Biopharmaceutics, vol. 110, pp. 58-69.

Sánchez-López et al., "Lipid nanoparticles (SLN, NLC): Overcoming the anatomical and physiological barriers of the eye—Part II—Ocular drug-loaded lipid nanoparticles," Jan. 2017, ScienceDirect, vol. 110, pp. 58-69. Abstract only.

* cited by examiner

*Primary Examiner* — Sean M Basquill
(74) *Attorney, Agent, or Firm* — Lee & Hayes, P.C.

(57) ABSTRACT

This invention relates to a Nanostructured Lipid Carrier (NLC) particle comprising a therapeutic agent encapsulated therein for ocular delivery of the therapeutic agent, wherein the Nanostructured Lipid Carrier comprises: (i) a solid outer shell comprising a solid lipid, and (ii) a liquid core comprising a liquid lipid; and wherein the core comprises the therapeutic agent. Compositions of the NLC particles, use of the NLC particles, methods of treatment or prevention of an eye disorder and an eye drop dispenser are also provided.

19 Claims, 31 Drawing Sheets

CHLF-D

CHLF

Figure 1:
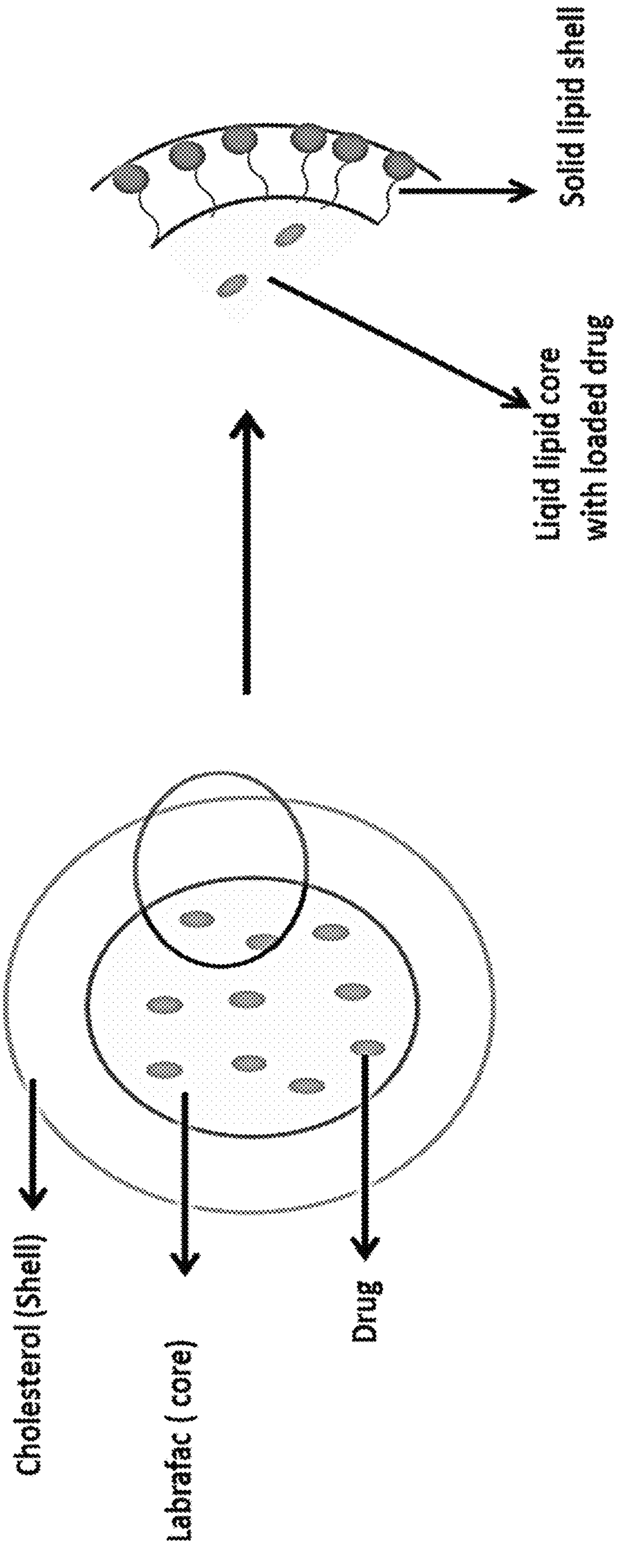

- Cell Line: Human Corneal Epithilium cells (HCEC)
- SAMPLE: FITC labelled CHLF NLC
- 4 Hour Post-transfection, Magnification: 10X

- CONTROL Cell without treatment of NLCs
- Cells with FITC labelled CHLF NLCs

- Pig Cornea
- SAMPLE: FITC labelled CHLF NLC
- 4 Hour Post-transfection, Magnification: 10X

- CONTROL Cornea without treatment of NLCs
- Cornea with FITC labelled CHLF NLCs Size and zeta potential of CHLF NLCs with and without drug loading

| SAMPLE NAME | DRUG CONTENT (mg/ml) | PARTICLE SIZE (nm) | ZETA POTENTIAL (mV) |
|---|---|---|---|
| CHLF 1:4 | 0 | 336 | -10.2 |
| CHLF-D 1:4 | 1 | 153.4 | -12.2 |

Mucoadhesion study by Fluorescence Microscopy

- Porcine eye cornea
- 4 Hour Incubation, Magnification: 10X
- Sample: Porcine eye cornea (Control)

Mucoadhesion study by Fluorescence Microscopy

- Porcine eye cornea
- 4 Hour Incubation, Magnification: 10X
- Sample: Porcine eye cornea (CHLF-CUMERIN 6 ENCAPSULATED SAMPLE)

Cellular uptake study by Fluorescence Microscopy

- Human Corneal Epithilium Cells (HCEC)
- 4 Hour Incubation, Magnification: 10X, 20X
- Sample:Control (No Treatment with nanoparticles)

Cellular uptake study by Fluorescence Microscopy

- Human Corneal Epithilium Cells (HCEC)
- 4 Hour Incubation, Magnification: 20X
- Sample:CHLF-CU6 ENCAPSULATED SAMPLE

OCULAR DRUG DELIVERY

This application is a continuation of U.S. application Ser. No. 16/955,336 filed Jun. 18, 2020 which is a U.S. National Phase Application of International Application No. PCT/IB2018/060528, filed Dec. 21, 2018, which claims priority to Great Britain Application No. GB 1721832.2, filed Dec. 22, 2017, which are incorporated herein by reference in their entirety.

The present invention relates to an encapsulated therapeutic agent for ocular delivery, and associated compositions, uses and treatments.

Ocular drug delivery is a major challenge faced by pharmaceutical scientists due to the eye's complexity and unique anatomy and physiology. Topical drug administration is the most convenient and patient compliant route of delivery, but inherent protective structural and physiological ocular features pose a barrier to delivery. Many topical drugs show poor bioavailability in the eye due to wash-off. In particular, one of the mechanisms responsible for poor bioavailability of drugs delivered to the eye is lacrimation. In addition, various layers of the cornea and sclera act as static barriers further limiting drug permeation.

Dexamethasone (DX) is an anti-inflammatory glucocorticoid and is a drug that can be used in the eye, for example to treat dry eye. DX is hydrophobic and faces extreme difficulty in penetration of the corneal epithelial barrier. There are various marketed emulsion-based eye drop formulations such as AzaSite®, Restasise™ and Refresh Endura®, the latter being a non-medicated emulsion. The major disadvantage of such formulations is that the concentration of the therapeutically active drug declines rapidly below the therapeutic index and repeated dosage is required. More than 80% of the applied dose can be removed due to lacrimal drainage. However, with frequent dosing there is a high risk of excessive drug concentration in the systemic circulation, which may result in toxicity.

The marketed emulsions also face instability, such as coalescence, flocculation and creaming. To prevent this instability they are typically formulated with surfactant, which results in increasing the kinetic stability of the emulsion. However, the addition of surfactant to emulsion is associated with cytotoxicity. In particular, it has been reported that suspension based formulations show disadvantages such as additive toxicity and blurred vision. To overcome these challenges a safer ophthalmic drug delivery strategy is needed.

There is need to overcome at least the above problems and to provide alternative, and preferably improved, methods and compositions for ophthalmic drug delivery and treatment.

According to the first aspect of the invention, there is provided a Nanostructured Lipid Carrier (NLC) particle comprising a therapeutic agent encapsulated therein for ocular delivery of the therapeutic agent, wherein the Nanostructured Lipid Carrier comprises:

(i) a solid outer shell comprising a solid lipid, optionally wherein the solid lipid comprises cholesterol; and (ii) a liquid core comprising a liquid lipid, optionally wherein the liquid lipid comprises a medium chain triglyceride, and wherein the core comprises the therapeutic agent.

The NLC particles according to the invention are advantageously nontoxic, biocompatible, and show favourable mucoadhesion, which result in an increase of residence time of the NLC particle on the cornea. Such advances lead to a favourable reduction of the dosage frequency. In particular, NLC particles according to the invention have shown efficient controlled therapeutic agent release. Ex vivo permeation studies also show efficient release of therapeutic agent.

In one embodiment, the solid lipid of the solid outer shell comprises or consists of cholesterol. In another embodiment, the solid lipid of the solid outer shell comprises or consists of a solid lipid selected from the group comprising tristearin, stearic acid, cetyl palmitate, cholesterol, glyceryl distearate NF/glyceryl palmitostearate (e.g. Precirol® ATO 5), esters of behenic acid with glycerol (e.g. Compritol® 888 ATO), tripalmitin (e.g. Dynasan®116), tristearin (e.g. Dynasan® 118), hydrogenated palm oil (e.g. Softisan® 154), cetyl palmitate (e.g. Cutina® CP), glyceryl stearate (e.g. Imwitor® 900 P), glycerol monostearate (e.g. Geleol®), glycerol monostearate and PEG-75 stearate (e.g. Gelot® 64), cetyl alcohol and ceteth-20/steareth-20 (e.g. Emulcire® 61) and cholesterol; or combinations thereof. Reference to a branded molecule/composition may be used interchangeably with the generic form thereof.

As cell membrane consists of lipid bilayer, the use of a solid lipid such as cholesterol will advantageously provide better diffusion of the NLC through the cell membrane.

The skilled person will recognise that medium-chain triglycerides (MCTs) are triglycerides whose fatty acids have an aliphatic tail of 6-12 carbon atoms. The fatty acids found in MCTs are called medium-chain fatty acids (MCFAs). In the case of MCTs, 2 or 3 of the fatty acid chains attached to glycerol are of medium length. The fatty acids may be saturated aliphatic acids, unsaturated aliphatic acids, or combinations thereof. In one embodiment, the fatty acids may comprise medium chain fatty acids, i.e. fatty acids having aliphatic tails of 6 to 12 carbons.

The medium chain triglycerides may comprise triglycerides of fatty acids selected from caproic acid, enanthic acid caprylic acid, nonanoic acid, capric acid, and lauric acid, or combinations thereof. The medium chain triglycerides may comprise triglycerides of capric acid (C10) and/or caprylic acid (C8). In one embodiment, the liquid lipid of the liquid core comprises or consists of Labrafac Lipophile® WL 1349. The skilled person will understand that Labrafac Lipophile® WL 1349 is a trade name for a medium-chain triglycerides of caprylic (C8) and capric (C10) acids. In one embodiment, the liquid lipid of the liquid core comprises or consists of 50% to 80% caprylic acid (C8) and 20% to 50% capric acid (C10). Other C6 to C14 lipids may also be provided in the liquid core, such as lauric acid (C12), caproic acid (C6), and myristic acid (C14). Such other C6 to C14 lipids, such as lauric acid (C12), caproic acid (C6), and myristic acid (C14), may be provided in the liquid core in amounts of 5% or less, 4% or less, 3% or less, 2% or less, or 1% or less, per component. In one embodiment, the liquid lipid of the liquid core comprises or consists of 50% to 80% caprylic acid (C8); 20% to 50% capric acid (C10); 2% or less caproic acid (C6); 3% or less of lauric acid (C12); and 1% or less myristic acid (C14). In one embodiment, the liquid lipid comprises medium chain triglycerides of capric acid (C10) and/or caprylic acid (C8) and the solid lipid comprises cholesterol. In one embodiment, the liquid lipid comprises Labrafac and the solid lipid comprises cholesterol.

In one embodiment, the liquid lipid of the liquid core comprises or consists of a lipid selected from the group comprising paraffin oil, 2-octyl dodecanol, oleic acid, squalene, isopropyl myristate, vitamin E, Miglyol® 812 (triglycerides of the fractionated plant fatty acids C8 and C10), diethylene glycol monoethyl ether NF (e.g. Transcutol® HP), Labrafac Lipophile® WL 1349 (medium chain triglycerides), propylene glycol dicaprylocaprate (e.g. Labrafac® PG), propylene glycol monolaurate (e.g. Lauroglycol® FCC), and propylene glycol monocaprylate (e.g. Capryol® 90), or combinations thereof. Reference to a branded molecule/composition may be used interchangeably with the generic form thereof.

In another embodiment, the liquid lipid of the liquid core may comprise or consist of Labrafil®. One or both of Labrafil® M 2125 CS (Linoleoyl Macrogol-6 glycerides) and Labrafil® M 1944 CS (Oleoyl macrogol-6 glycerides) may be suitable as the liquid lipid of the liquid lipid core. It is understood that Labrafil® M 2125 CS consists of mono-, di- and triglycerides and PEG-6 (MW 300) mono- and diesters of linoleic ($C_{18:2}$) acid and Labrafil® M 1944 CS consists of mono-, di- and triglycerides and PEG-6 (MW 300) mono- and diesters of oleic ($C_{18:1}$) acid.

The medium chain triglyceride, such as Labrafac™ Lipophile WL1349, advantageously acts as a penetration enhancer and facilitates the release of the therapeutic agent in the cytoplasm of corneal cells.

In another embodiment, the liquid lipid of the liquid lipid core comprises coconut oil. In another embodiment, the liquid lipid of the liquid lipid core may comprise a synthetic equivalent of coconut oil or one or more components of coconut oil. The liquid lipid may comprise a fraction of coconut oil. The coconut oil, also referred to as copra oil, may comprise the medium chain triglycerides caprylic acid, capric acid, caproic acid, and lauric acid. Therefore, the liquid lip may comprise one or more, or all of, caprylic acid, capric acid, caproic acid, and lauric acid. The coconut oil may further comprise other lipids such as myristic acid, palmitic acid, stearic acid, arachidic acid, oleic acid, and linoleic acid. Therefore, the liquid lip may additionally or alternatively comprise one or more, or all of, myristic, palmitic acid, stearic acid, arachidic acid, oleic acid, and linoleic acid. Therefore, the liquid lip may comprise one or more medium chain triglycerides that are the majority constituents of coconut oil. In one embodiment, the liquid lipid of the liquid core comprises or consists of a coconut oil component selected from the group comprising caproic acid (C6), caprylic acid (C8), capric acid (C10), lauric acid (C12), myristic acid (C14), palmitic acid (C16), stearic acid (C18), arachidic acid (C20), oleic acid (C18), and linoleic acid (C18); or combinations thereof. In one embodiment, the liquid lipid of the liquid core comprises or consists of 0.2% to 0.5% caproic acid (C6), 5.4% to 9.5% caprylic acid (C8), 4.5% to 9.7% capric acid (C10), 44.1% to 51.3% lauric acid (C12), 13.1% to 18.5% myristic acid (C14), 7.5% to 10.5% palmitic acid (C16), 1.0% to 3.2% stearic acid (C18), less than 1.5% arachidic acid (C20), 5.0% to 8.2% oleic acid (C18), and 1.0% to 2.6% linoleic acid (C18). It is understood that the percentage amounts refer to the amount provided in the coconut oil, or equivalent, fraction or component thereof, prior to formulating into the lipid liquid core (i.e. the starting amount). Therefore, if the coconut oil, or equivalent, fraction or component thereof, is provided with another liquid lipid composition in the liquid lipid core then the above percentages may be diluted accordingly. For example if the coconut oil, or equivalent, fraction or component thereof, is provided in a 1:1 ratio with another liquid lipid such as castor oil, or equivalent, fraction or component thereof, then the above percentage amounts would be halved.

Advantageously, coconut oil has anti-inflammatory, antibacterial, and antifungal properties. Furthermore, it may provide a soothing effect to eyes and reduce the evaporation of tears from the eye.

In another embodiment, the liquid lipid of the liquid lipid core comprises castor oil. In another embodiment, the liquid lipid of the liquid lipid core may comprise a synthetic equivalent of castor oil or one or more components of castor oil. The liquid lipid may comprise a fraction of castor oil. The castor oil may comprise the lipids ricinoleic acid, linoleic acid, oleic acid, stearic acid, palmitic acid, dihydroxystearic acid, and linolenic acid. Therefore, the liquid lip may comprise one or more, or all of, ricinoleic acid, linoleic acid, oleic acid, stearic acid, palmitic acid, dihydroxystearic acid, and linolenic acid. In one embodiment, the liquid lipid of the liquid core comprises or consists of castor oil component selected from the group comprising ricinoleic acid (C18), linoleic acid (C18), oleic acid (C18), stearic acid (C18), palmitic acid (C16), dihydroxystearic acid (C18), and linolenic acid (C18). In one embodiment, the liquid lipid of the liquid core comprises or consists of castor oil which comprises 85% to 95% ricinoleic acid (C18), 1% to 5% linoleic acid (C18), 2% to 6% oleic acid (C18), 0.5% to 1% stearic acid (C18), 0.5% to 1% palmitic acid (C16), 0.3% to 0.5% dihydroxystearic acid (C18), and 0.5% to 1% linolenic acid (C18). It is understood that the percentage amounts refer to the amount provided in the castor oil, or equivalent, fraction or component thereof, prior to formulating into the lipid liquid core (i.e. the starting amount). Therefore, if the castor oil, or equivalent, fraction or component thereof, is provided with another liquid lipid composition in the liquid lipid core then the above percentages may be diluted accordingly. For example if the castor oil, or equivalent, fraction or component thereof, is provided in a 1:1 ratio with another liquid lipid such as coconut oil, or equivalent, fraction or component thereof, then the above percentage amounts would be halved.

Advantageously, castor oil has anti-inflammatory properties, reduces the evaporation of tears from the eye and is suitable for the treatment of Meibomian gland dysfunction.

In a further embodiment, the liquid lipid of the liquid lipid core comprises both coconut oil, or equivalent, fraction or component thereof, and castor oil, or equivalent, fraction or component thereof. The coconut oil, or equivalent, fraction or component thereof, and castor oil, or equivalent, fraction or component thereof, may be provided in a ratio of about 1:1. The coconut oil, or equivalent, fraction or component thereof, and castor oil, or equivalent, fraction or component thereof, may be provided in a ratio of between about 0.8:1.2 and about 1.2:0.8. In another embodiment the coconut oil, or equivalent, fraction or component thereof, and castor oil, or equivalent, fraction or component thereof, may be provided in a ratio of between about 0.5:1.5 and about 1.5:0.5.

Advantageously, coconut oil and castor oil (or equivalents, fractions or components thereof) act as penetration enhancers and facilitate the release of the therapeutic agent in the cytoplasm of corneal cells.

In one embodiment, the liquid lipid comprises castor oil or equivalents, fractions or components thereof, and coconut oil or equivalents, fractions or components thereof; and the solid lipid comprises cholesterol. In one embodiment, the liquid lipid comprises castor oil or equivalents, fractions or components thereof, and coconut oil or equivalents, fractions or components thereof, in about 1:1 ratio; and the solid lipid comprises cholesterol. In one embodiment, the liquid lipid comprises castor oil and coconut oil; and the solid lipid comprises cholesterol. In one embodiment, the liquid lipid comprises castor oil and coconut oil in about 1:1 ratio; and the solid lipid comprises cholesterol.

In one embodiment, the therapeutic agent is suitable for treatment or prevention of an eye disorder. The eye disorder may comprise any one of the disorders selected from dry eye syndrome (keratoconjunctivitis sicca); conjunctivitis; keratitis; uveitis; scelritis; episcleritis; blepharitis; *Acanthamoeba keratitis*; and iritis; or combinations thereof. In one embodiment, the therapeutic agent is suitable for treatment or prevention of dry eye.

The therapeutic agent may be hydrophobic. In one embodiment, the therapeutic agent is an anti-inflammatory agent. In one embodiment, the anti-inflammatory agent is dexamethasone. The anti-inflammatory agent may comprise or consist of a corticosteroid, such as dexamethasone. In another embodiment, the corticosteroid may be selected from the group comprising fluocinolone, difluprednate, loteprednol, fluorometholone, medrysone, dexamethasone, prednisolone, triamcinolone, and rimexolone, or combinations thereof. The therapeutic agent may comprise an antihistamine and/or decongestant.

The therapeutic agent may be provided at a concentration of between about 0.01 mg/ml and about 1 mg/ml. In another embodiment, the therapeutic agent may be provided at a concentration of between about 0.01 mg/ml and about 0.5 mg/ml. In another embodiment, the therapeutic agent may be provided at a concentration of between about 0.05 mg/ml and about 1 mg/ml. In another embodiment, the therapeutic agent may be provided at a concentration of between about 0.1 mg/ml and about 1 mg/ml. In another embodiment, the therapeutic agent may be provided at a concentration of between about 0.2 mg/ml and about 1 mg/ml. In another embodiment, the therapeutic agent may be provided at a concentration of between about 0.5 mg/ml and about 1 mg/ml. In another embodiment, the therapeutic agent may be provided at a concentration of between about 0.01 mg/ml and about 0.2 mg/ml. In another embodiment, the therapeutic agent may be provided at a concentration of between about 0.5 mg/ml and about 1 mg/ml. The concentration of the therapeutic agent in the core may refer to the total concentration in a suspension of the NLC particles.

The therapeutic agent may be provided in combination with one or more other therapeutically active agents. For example, a second, third or more therapeutic agent may be provided in the core and/or outer shell. The second, third or more therapeutic agent may comprise an antibiotic.

The Nanostructured Lipid Carrier particle may be of nanoparticle size. In one embodiment, the Nanostructured Lipid Carrier particle is less than about 1000 nm at its largest diameter. In another embodiment, the Nanostructured Lipid Carrier particle is less than about 800 nm at its largest diameter. In another embodiment, the Nanostructured Lipid Carrier particle is less than about 800 nm at its largest diameter. In another embodiment, the Nanostructured Lipid Carrier particle is less than about 700 nm at its largest diameter. In another embodiment, the Nanostructured Lipid Carrier particle is less than about 600 nm at its largest diameter. In another embodiment, the Nanostructured Lipid Carrier particle is less than about 500 nm at its largest diameter. In another embodiment, the Nanostructured Lipid Carrier particle is less than about 400 nm at its largest diameter. In another embodiment, the Nanostructured Lipid Carrier particle is less than about 300 nm at its largest diameter. In another embodiment, the Nanostructured Lipid Carrier particle is less than about 200 nm at its largest diameter. In another embodiment, the Nanostructured Lipid Carrier particle is less than about 200 nm at its largest diameter. In another embodiment, the Nanostructured Lipid Carrier particle is less than about 50 nm at its largest diameter. In another embodiment, the Nanostructured Lipid Carrier particle is less than about 200 nm at its largest diameter. In another embodiment, the Nanostructured Lipid Carrier particle is between about 15 nm and about 1000 nm at its largest diameter. In another embodiment, the Nanostructured Lipid Carrier particle is between about 15 nm and about 800 nm at its largest diameter. In another embodiment, the Nanostructured Lipid Carrier particle is between about 15 nm and about 500 nm at its largest diameter. In another embodiment, the Nanostructured Lipid Carrier particle is between about 15 nm and about 100 nm at its largest diameter. In another embodiment, the Nanostructured Lipid Carrier particle is between about 15 nm and about 50 nm at its largest diameter. In another embodiment, the Nanostructured Lipid Carrier particle is between about 15 nm and about 30 nm at its largest diameter. In another embodiment, the Nanostructured Lipid Carrier particle is between about 19 nm and about 21 nm at its largest diameter. The Nanostructured Lipid Carrier particle may be substantially spherical in shape.

In one embodiment, the NLC particle comprises about 1:30 or 1:4 of solid outer shell relative to liquid core. Alternatively, the NLC may comprise between about 1:4 and about 1:30 of solid outer shell relative to liquid core. Alternatively, the NLC may comprise between about 1:3.5 and about 1:5 of solid outer shell relative to liquid core. In another embodiment, the NLC may comprise between about 1:35 and about 1:4.5 of solid outer shell relative to liquid core. In another embodiment, the NLC may comprise between about 1:25 and about 1:35 of solid outer shell relative to liquid core. In another embodiment, the NLC may comprise between about 1:28 and about 1:35 of solid outer shell relative to liquid core. In another embodiment, the NLC may comprise between about 1:28 and about 1:32 of solid outer shell relative to liquid core. The percentage v/w of liquid core of an NLC particle may be an average in a population of NLCs.

According to another aspect of the invention, there is provided a composition comprising a plurality of NLC particles comprising a therapeutic agent encapsulated therein in accordance with the invention herein.

The composition may be a pharmaceutically acceptable composition. The composition may be an ophthalmically acceptable composition. For example, the NLC particles may be provided in a pharmaceutically acceptable carrier. The pharmaceutically acceptable carrier may be an ophthalmically acceptable carrier. The composition may be suitable for topical administration to the eye. In one embodiment, the composition is an ophthalmic composition. An ophthalmic composition is understood to be a sterile, liquid, semi-solid, or solid preparation that may contain one or more active pharmaceutical ingredient(s) (i.e. the anti-inflammatory agent described herein) intended for application to the eye or eyelid.

The composition may be in the form of the NLC particles suspended in a gel, lotion, cream, ointment, or solution, such as an aqueous solution. In one embodiment, the composition is in the form of an eye drop formulation.

The composition may comprise one or more ophthalmically acceptable ingredients selected from the group consisting of: water; saline; salt; buffer; demulcent; humectant; viscosity increasing agent; tonicity adjusting agent; cellulose derivatives e.g. carboxymethylcellulose sodium, hydroxyethyl cellulose, hydroxypropyl methylcellulose, or methylcellulose; dextran 70; gelatin; polyols; glycerine; polyethylene glycol e.g. PEG300 or PEG400; polysorbate 80; propylene glycol; polyvinyl alcohol; and povidone (polyvinyl pyrrolidone); and combinations thereof.

Demulcents may comprise or consist of cellulose derivatives, glycerine, polyvinyl alcohol, polyvinyl pyrrolidone, cellulose derivatives, polyethylene glycol, or combinations thereof.

In one embodiment, the carrier of the NLC particles in the composition, does not substantially comprise a surfactant. In one embodiment, the carrier of the NLC particles in the composition, does not comprise a physiologically relevant concentration of surfactant. In one embodiment, the carrier of the NLC particles in the composition comprises no more than 0.05% or no more than 1% of a surfactant, such as polysorbate/Tween 80.

According to another aspect of the present invention, there is provided a composition according to the invention herein for use in the treatment or prevention of an eye disorder in a subject.

According to another aspect of the present invention, there is provided the use of a composition according to the invention herein in the manufacture of a medicament for treatment or prevention of an eye disorder in a subject.

According to another aspect of the present invention, there is provided a method of treatment or prevention of an eye disorder in a subject comprising the administration of the composition according to the invention to an eye of the subject.

The administration may be topical to the surface of the eye or to the eyelid.

The subject may be mammalian. In one embodiment, the subject is a human subject. The subject may be in need of treatment for the eye disorder or may be at risk of developing the eye disorder. The subject may be a non-human animal, such as a domestic animal or livestock. In one embodiment, the use of the invention may be veterinary.

The administration of the composition may be a pharmaceutically effective amount of the composition. The treatment or prevention may comprise a single administration or repeated administrations. The administration may be once every 1 to 18 days. The administration may be once every 5 to 18 days. The administration may be once every 7 to 18 days. The administration may be once every 10 to 18 days. The administration may be once every 15 to 18 days. The administration may be about once every 7 days. The administration may be no more than once per day.

The eye disorder may be selected from dry eye syndrome (keratoconjunctivitis sicca), conjunctivitis, keratitis, uveitis, scelritis, episcleritis, blepharitis, *acanthamoeba keratitis*, dacryostenosis, dacryocystitis, and iritis; or combinations thereof. The disorder may be acute or chronic.

In another aspect of the invention, there is provided an eye drop dispenser or eye wash device comprising the composition according to the invention herein.

An eye drop dispenser may otherwise be known as an eye drop applicator. Typical eye drop dispensers comprise a reservoir for the composition and an outlet for the composition. The outlet may be tapered towards a distal end, with the outlet orifice at the tip/distal end. The dispenser may be arranged to be sealed, for example with a cap. An eye drop dispenser may alternatively comprise a syringe device.

The skilled person will be familiar with the term "Nanostructured Lipid Carrier (NLC)" where it is intended to refer to a drug-delivery system composed of both solid and liquid lipids as a core matrix.

The term "solid" in the context of the solid outer shell is understood to mean solid at room temperature (i.e. about 24° C.). i.e. the outer shell is solid at room temperature. The term "liquid" in the context of the liquid core is understood to mean liquid at room temperature (i.e. about 24° C.). i.e. the core is liquid at room temperature. In one embodiment, the solid outer shell of the NLC particles is solid at body temperature (e.g. 37° C.).

The term "solid" in the context of the solid lipid is understood to mean a composition of the lipid is a solid at room temperature (i.e. about 24° C.), i.e. the lipid exists as a solid at room temperature. In one embodiment, the solid lipid forms a solid at body temperature (e.g. 37° C.). The term "liquid" in the context of the liquid lipid is understood to mean a composition of the lipid is a liquid at room temperature (i.e. about 24° C.), i.e. the lipid exists as a liquid at room temperature.

The term "prevention" means avoidance of a disorder or a protective treatment for a disorder. The prevention may include a reduced risk of the disorder, reduced risk of infection, transmission and/or progression, or reduced severity of the disorder.

The term "treatment" means a cure of a condition or disease, an alleviation of symptoms, or a reduction in severity of a disorder or symptoms of the disorder.

The skilled person will understand that optional features of one embodiment or aspect of the invention may be applicable, where appropriate, to other embodiments or aspects of the invention.

Embodiments of the invention will now be described in more detail, by way of example only, with reference to the accompanying drawings.

FIG. 1. Schematic illustrating the structure of the DX encapsulated CHLF-NLCs. NLCs mainly consist of lipids e.g. Solid lipid (outer layer) and liquid lipid (core). The drug is encapsulated in Liquid lipid. Cholesterol is solid lipid and Labrafac Lipophile® WL 1349 is liquid lipid with drug is encapsulated in the liquid lipid.

Figure 2:
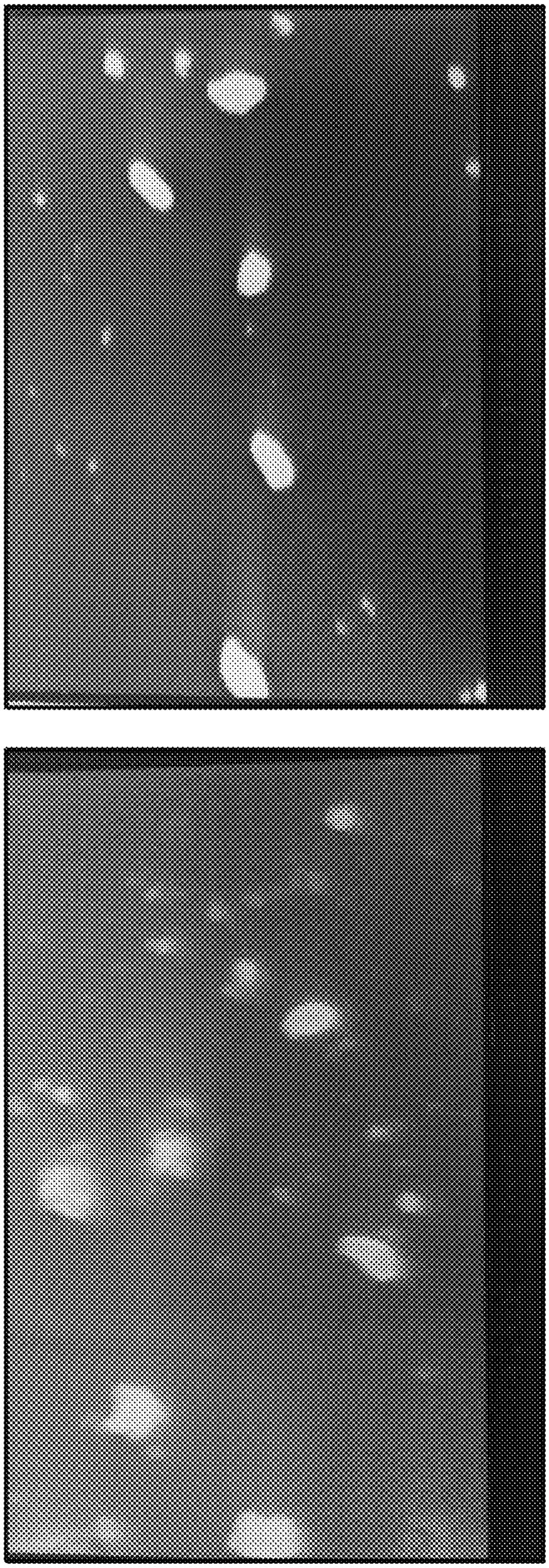

FIG. 2. SEM images of CHLF-NLCs with (CHLF-D) and without (CHLF) drug loading.

Figure 3:
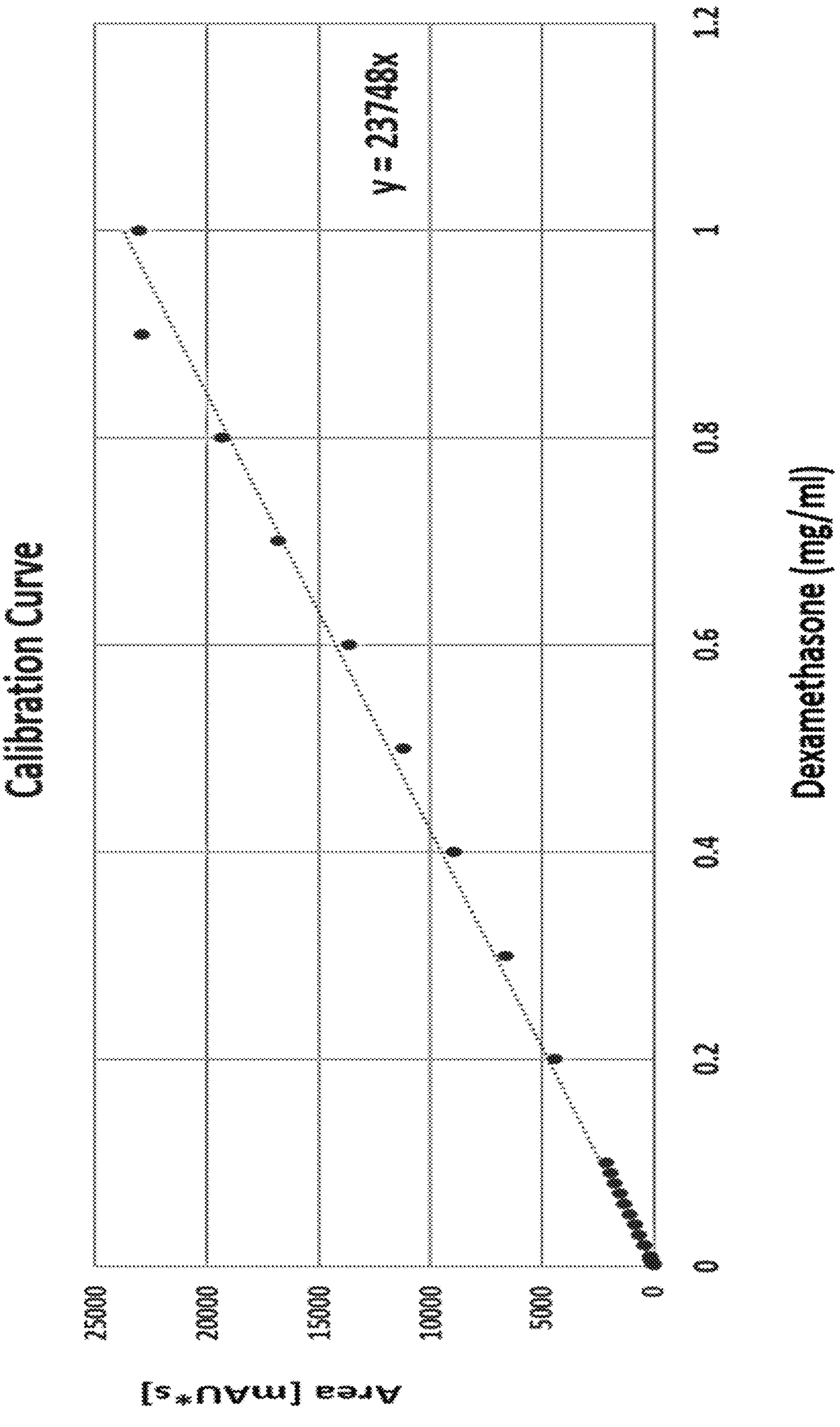

FIG. 3. Calibration curve for the dexamethasone and calculated drug entrapment efficiency of CHLF-D. Percentage entrapment efficiency for CHLF-D (1:30) (1 mg/ml): 99.9%.

Figure 4:
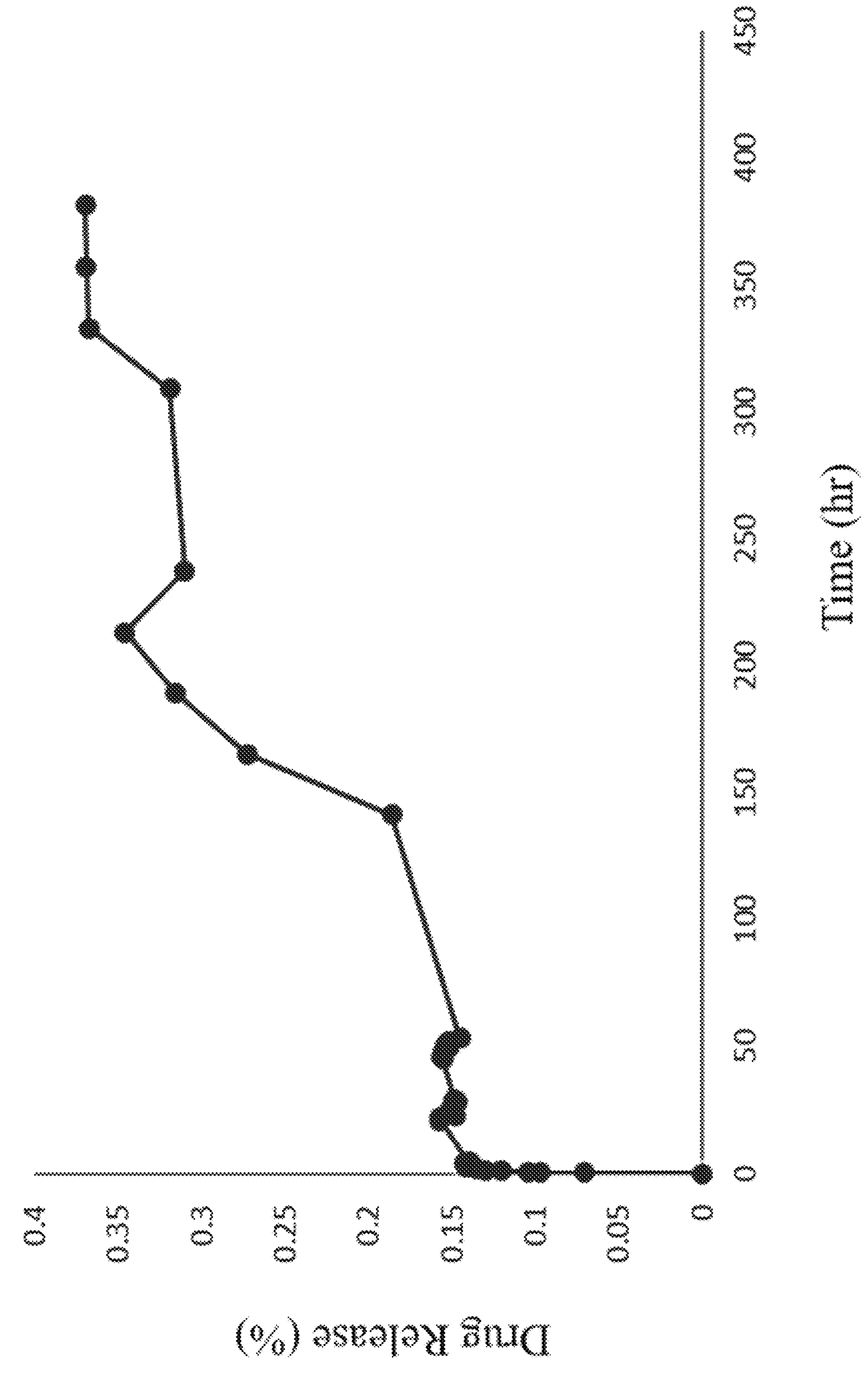

FIG. 4. Dexamethasone release study from the CHLF-NLCs.

Figure 5:
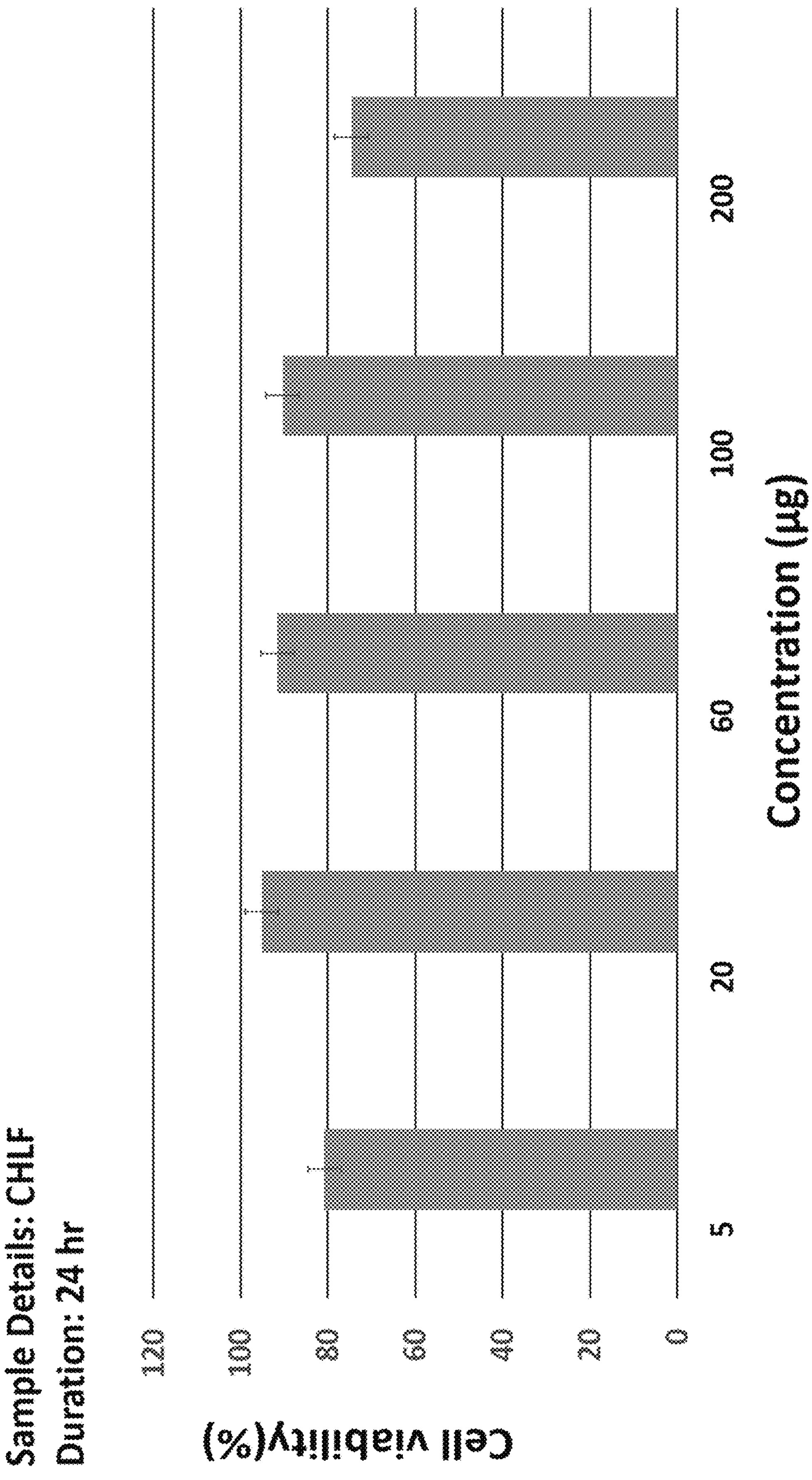

FIG. 5. Cytotoxicity study of CHLF NLCs ratio (1:30) with MTT assay.

Figure 6:
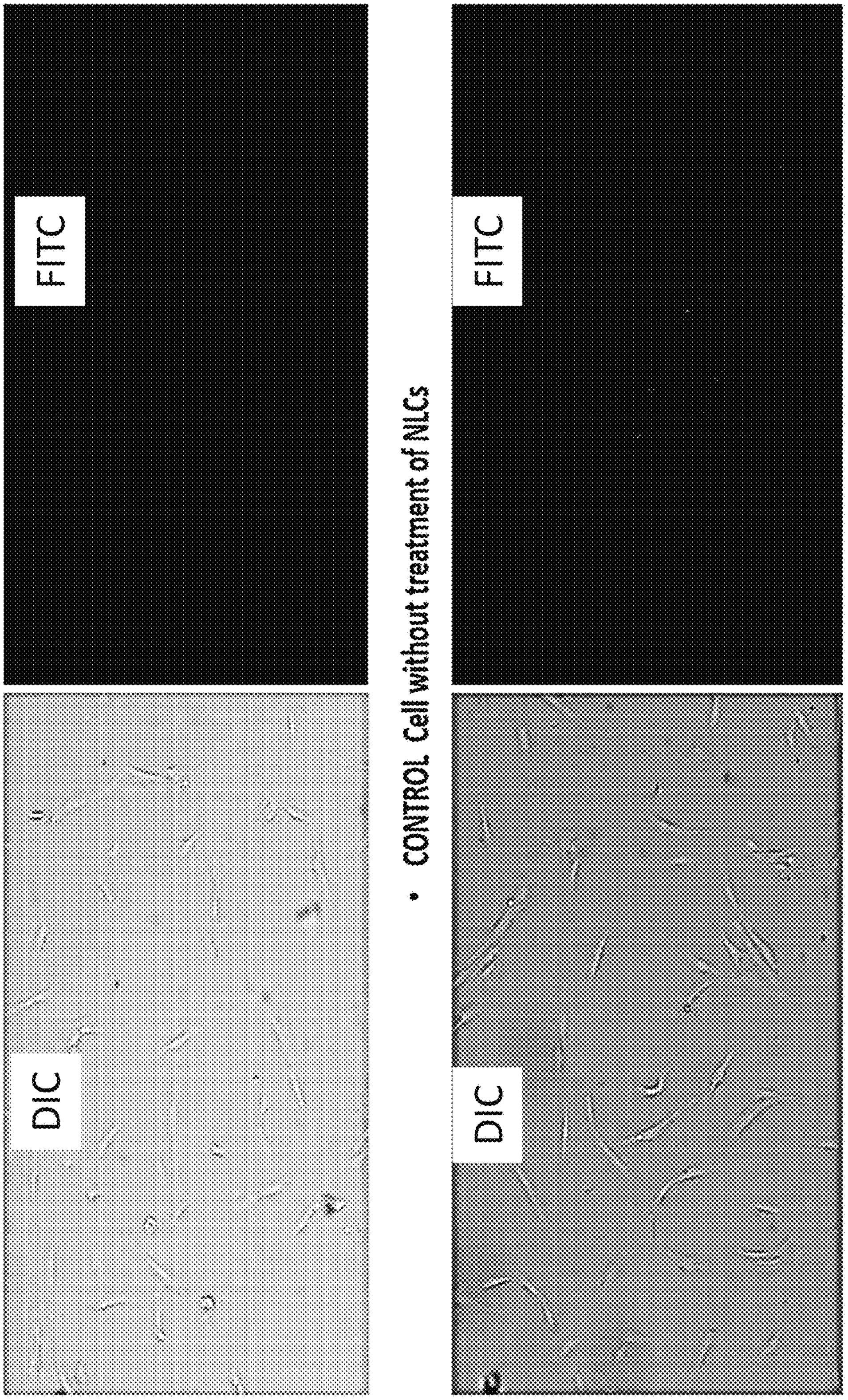

FIG. 6. Cellular uptake study of CHLF-NLC with fluorescence microscopy.

Figure 7:
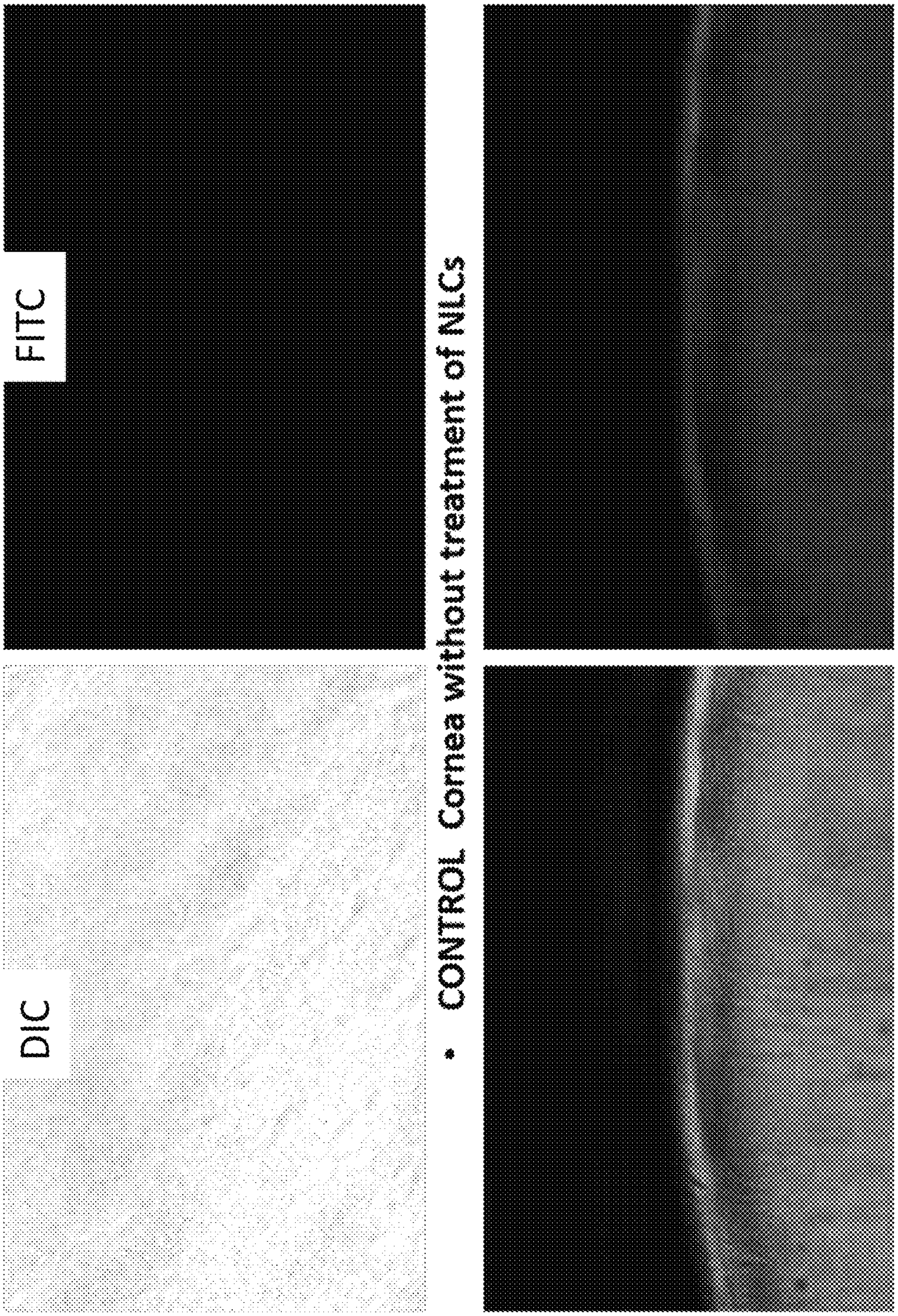

FIG. 7. Ex vivo mucoadhesion study with fluorescence Microscopy.

Figure 8:
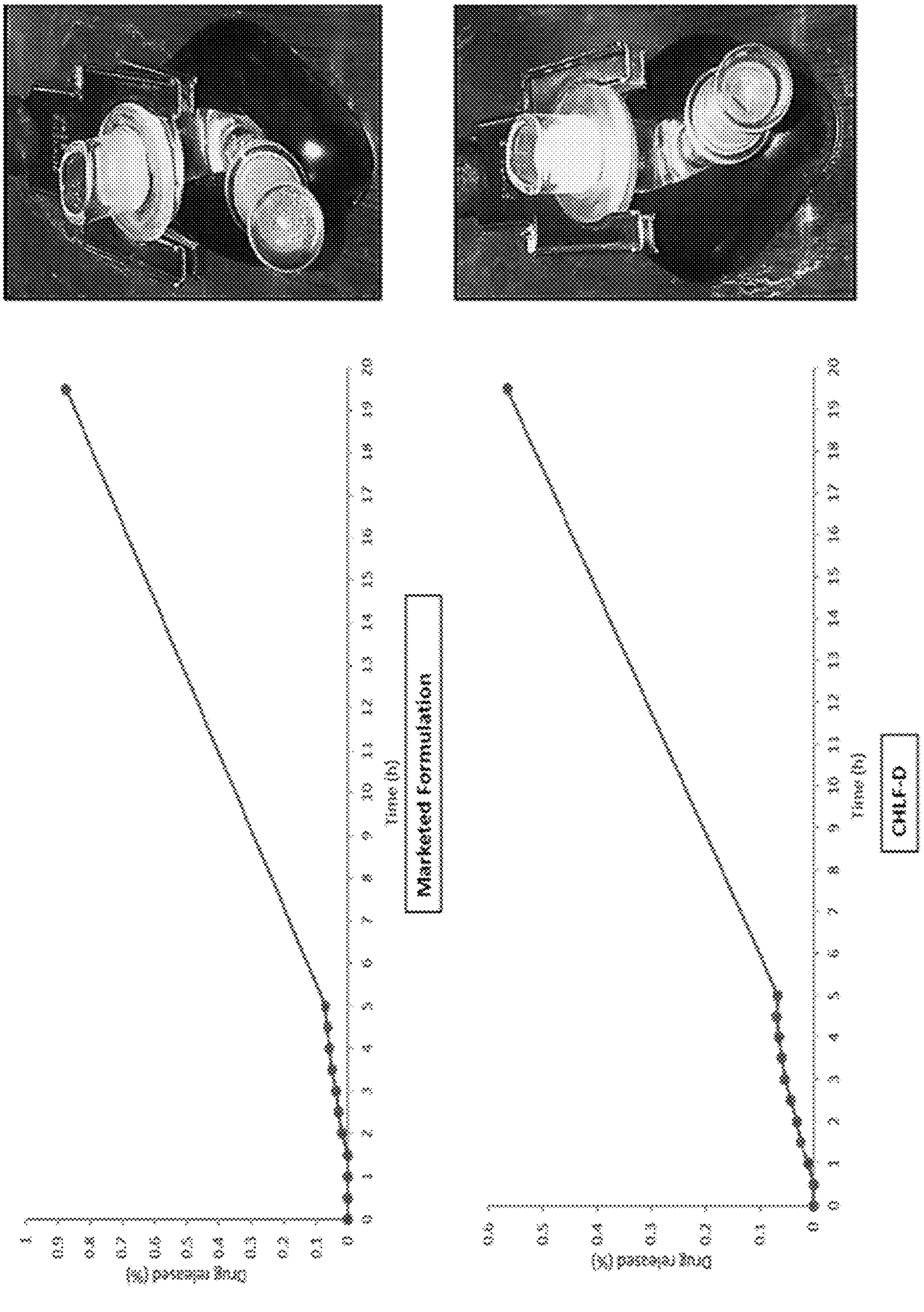

FIG. 8. Permeation study with drug loaded CHLF NLCs and marketed formulation MAXIDEX.

Figures 9, 10:
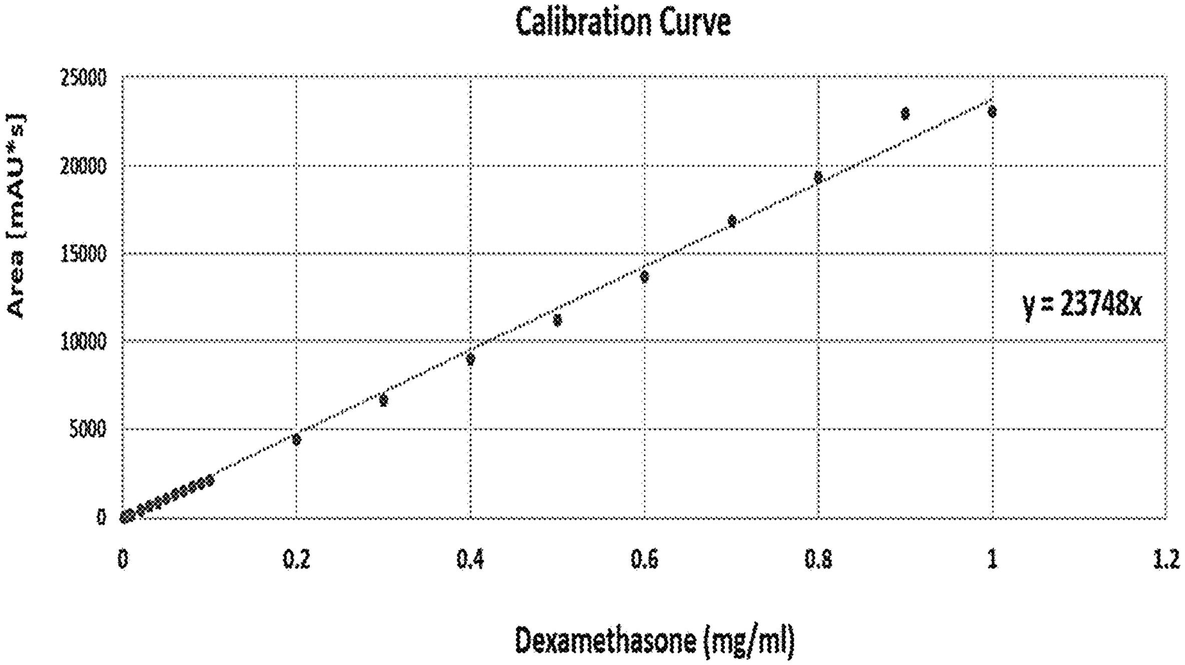

FIG. 9. Size and zeta potential of CHLF (without drug loaded) NLC and CHLF-D (with drug loaded) NLC of 1:4 ratio.

FIG. 10. Calibration curve for the dexamethasone and calculated drug entrapment efficiency of CHLF-D. Percentage entrapment efficiency for CHLF-D (1:4) (1 mg/ml): 99.67%.

Figure 11:
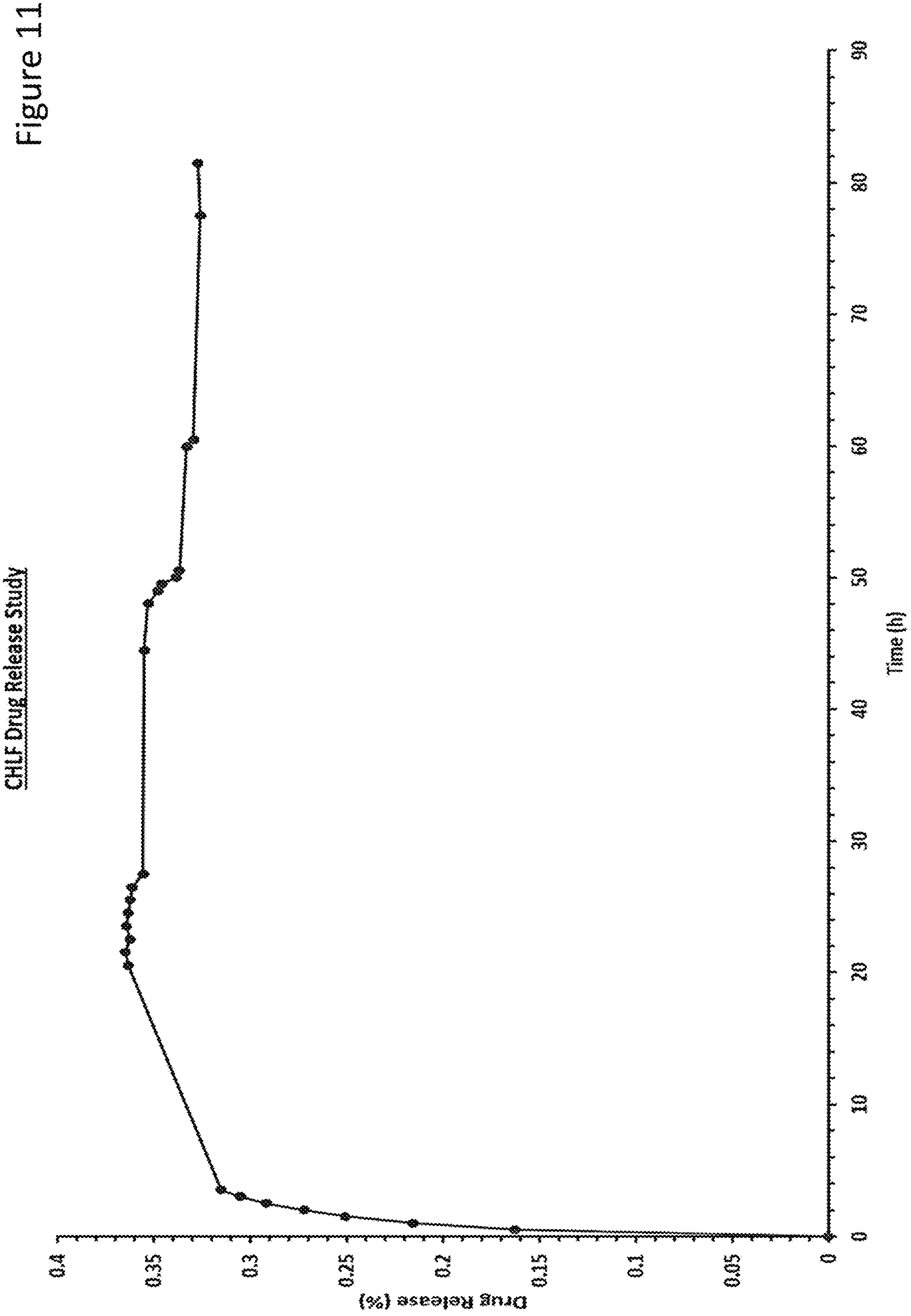

FIG. 11. Dexamethasone release study from the CHLF-D (1:4) NLCs.

Figure 12:
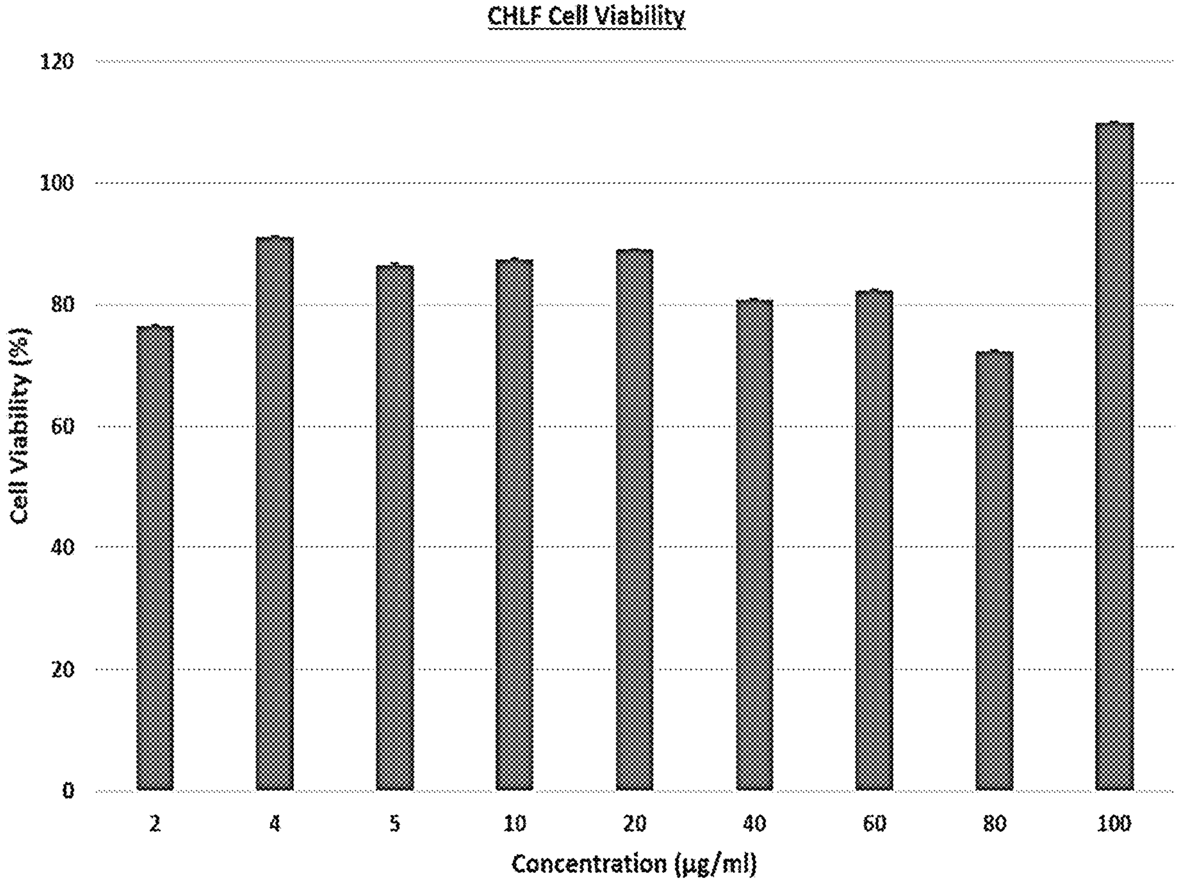

FIG. 12. Cytotoxicity study of CHLF (1:4) NLCs with MTT assay.

Figure 13:
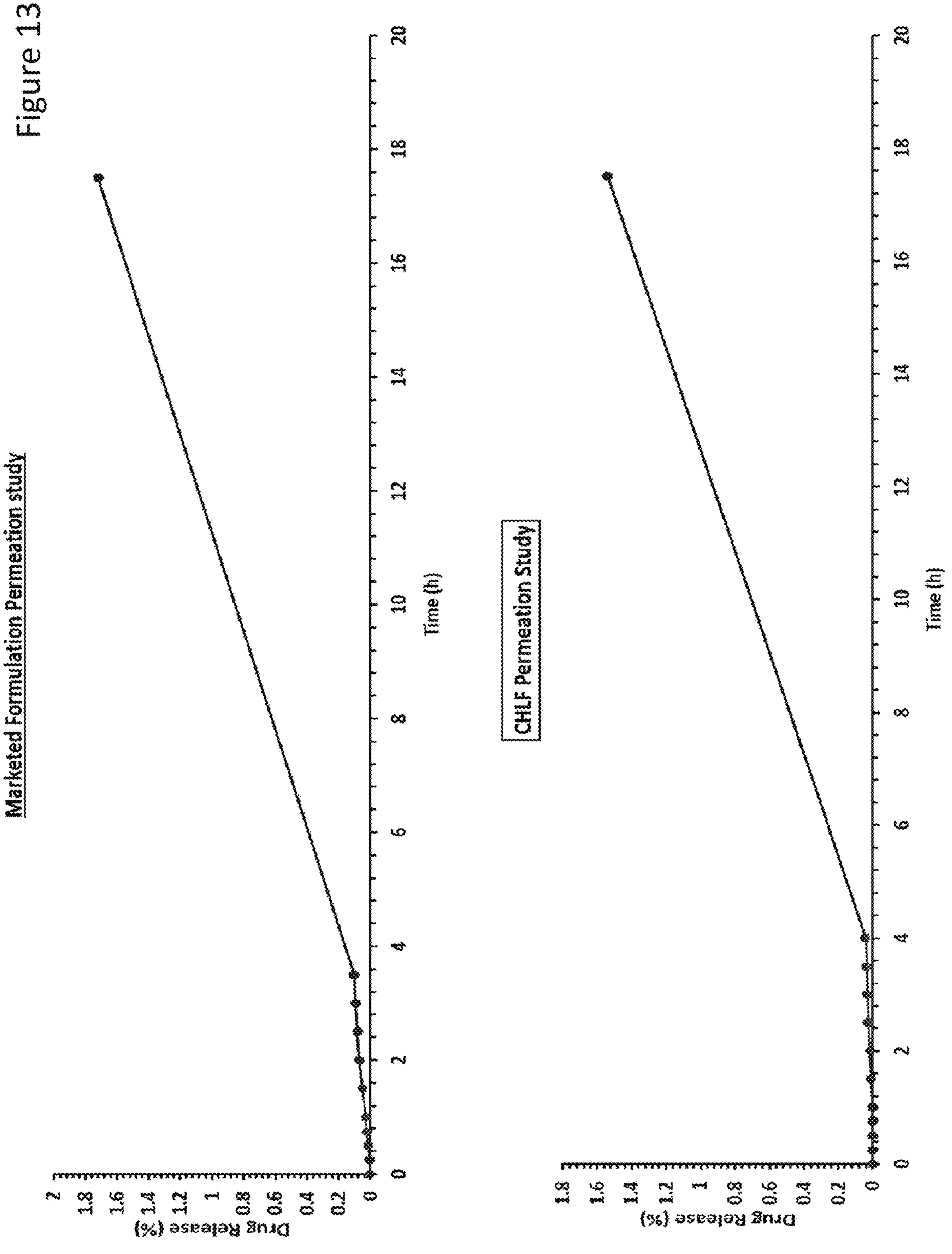

FIG. 13. Permeation study with drug loaded CHLF (1:4) NLCs and marketed formulation MAXIDEX.

Figure 14:
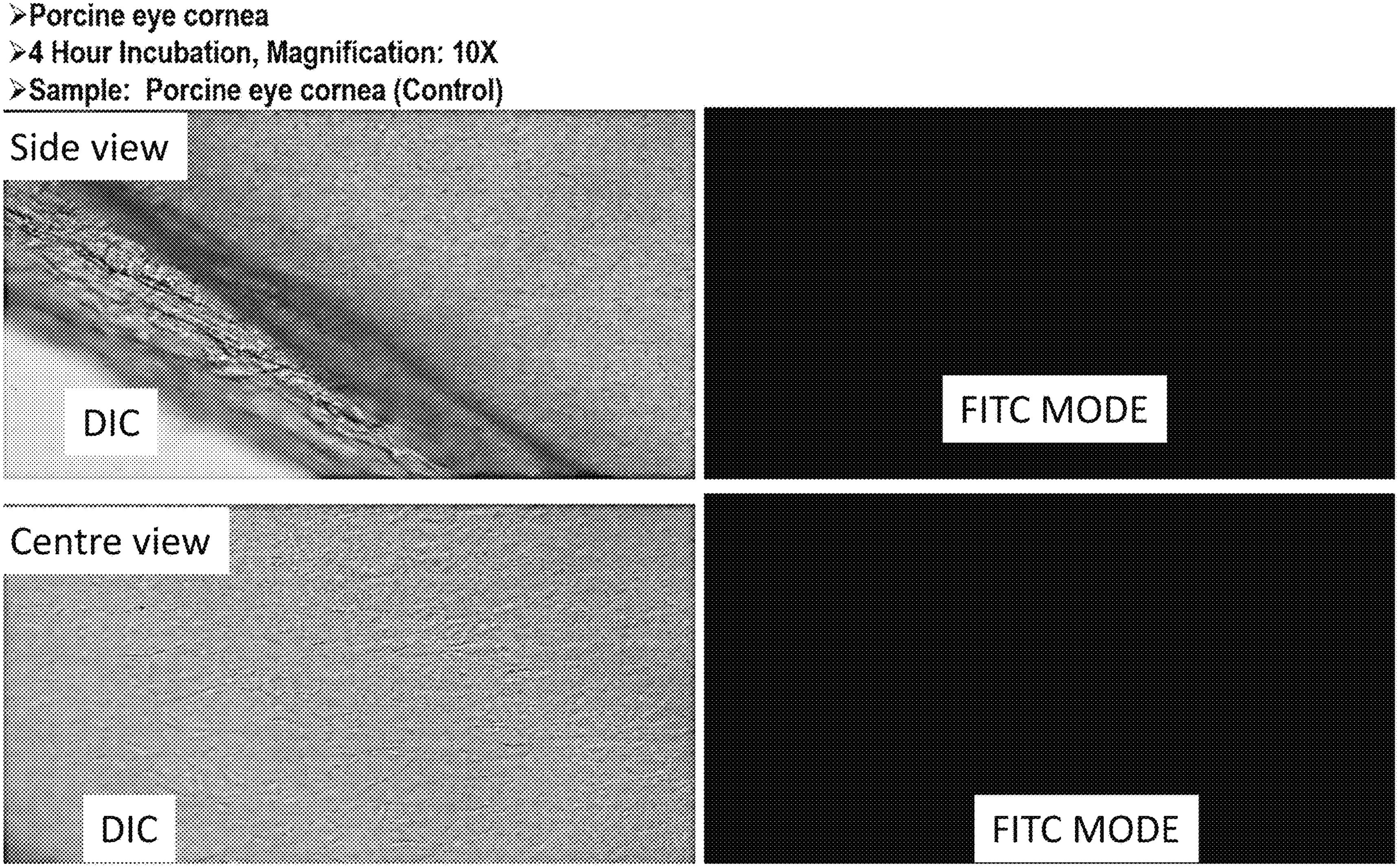

FIG. 14. Ex vivo mucoadhesion study by fluorescence Microscopy of without CHLF-NLC treated cornea.

Figure 15:
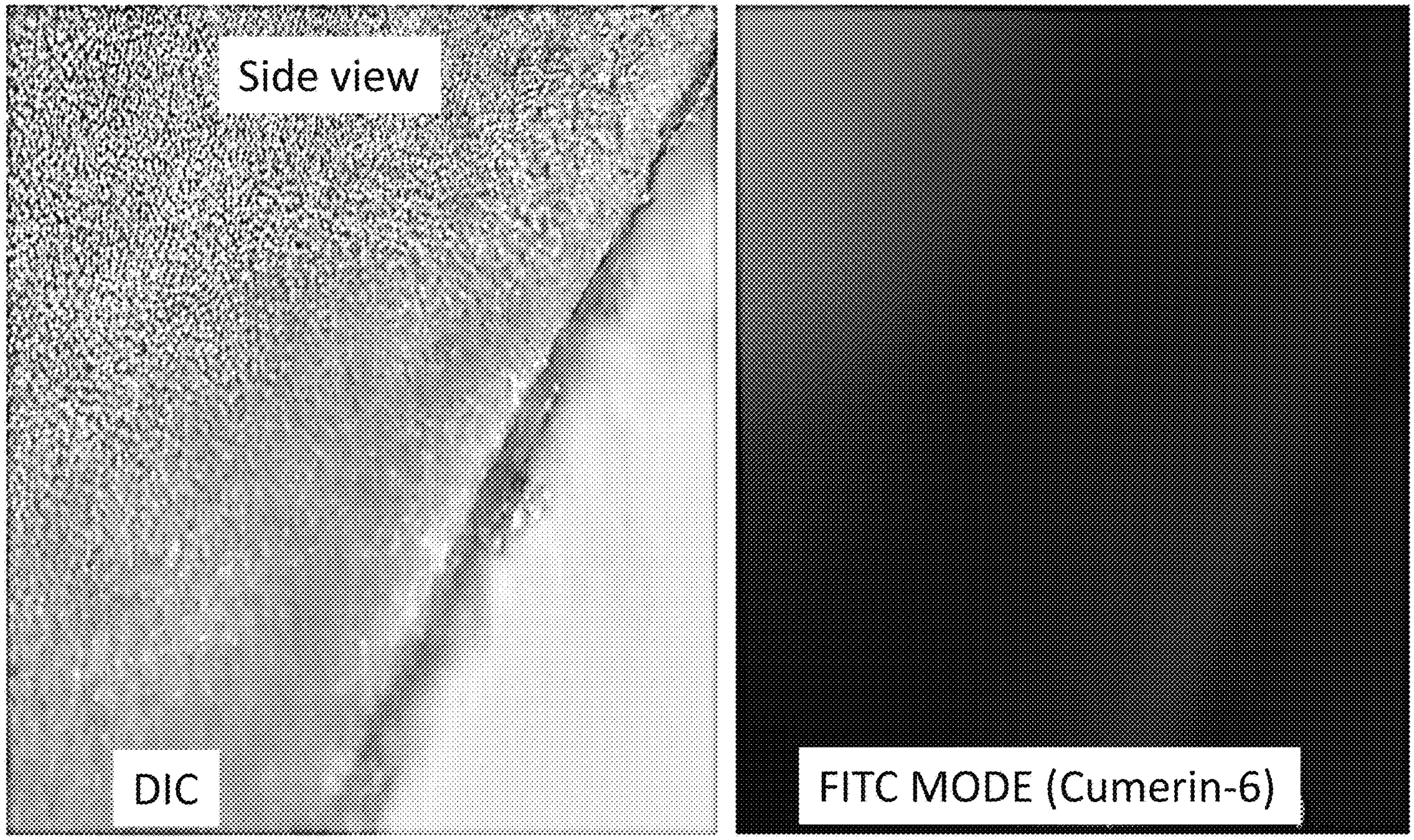

FIG. 15. Ex vivo mucoadhesion study by fluorescence Microscopy of Coumarin-6 labelled CHLF-NLC treated cornea.

Figure 16:
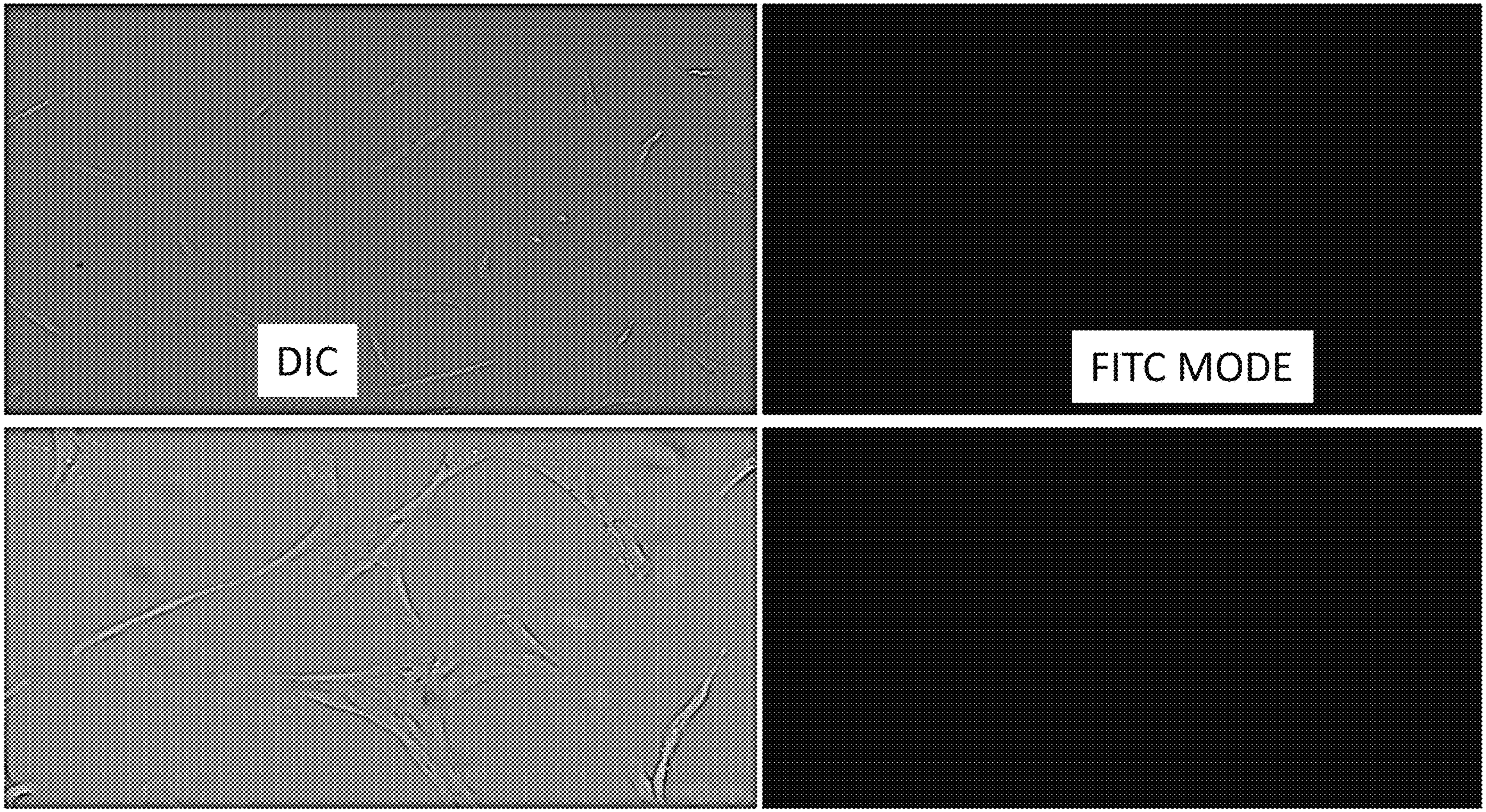

FIG. 16. Cellular uptake study by fluorescence microscopy of human corneal epithelium cells without CHLF-NLC treatment.

Figure 17:
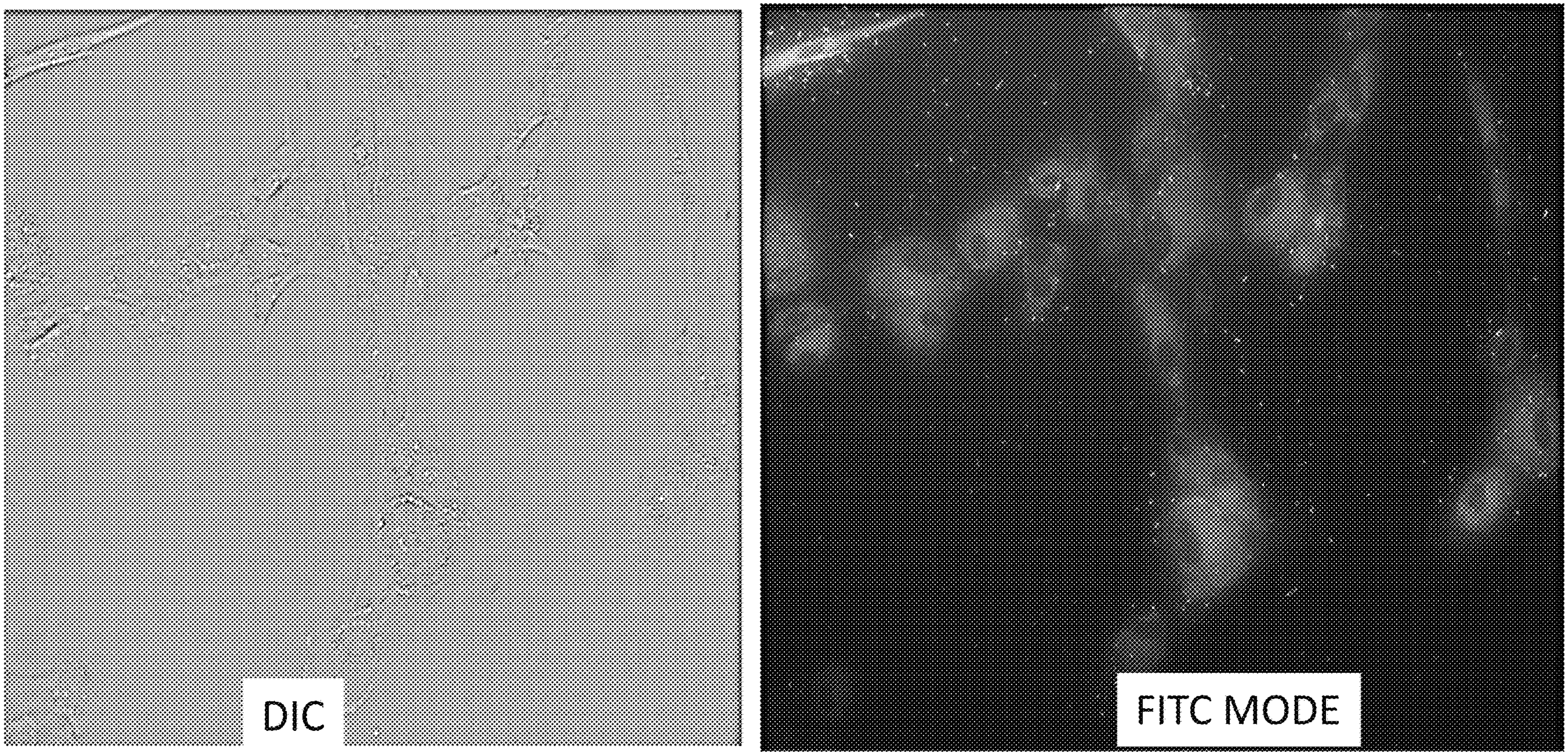

FIG. 17. Cellular uptake study by fluorescence microscopy of human corneal epithelium cells with Cumarin 6 encapsulated CHLF-NLC treatment.

Figure 18:
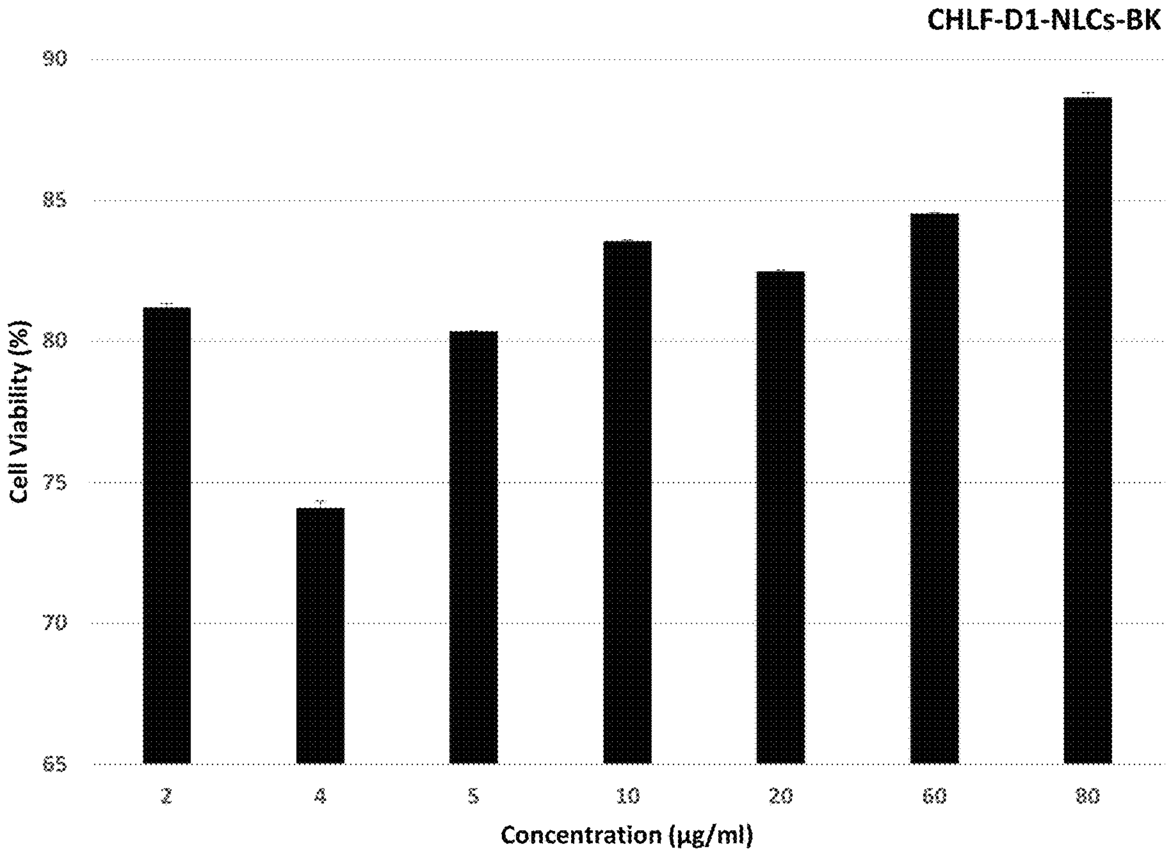

FIG. 18. Cell viability study of pilot scale CHLF-D-NLCs.

Figure 19:
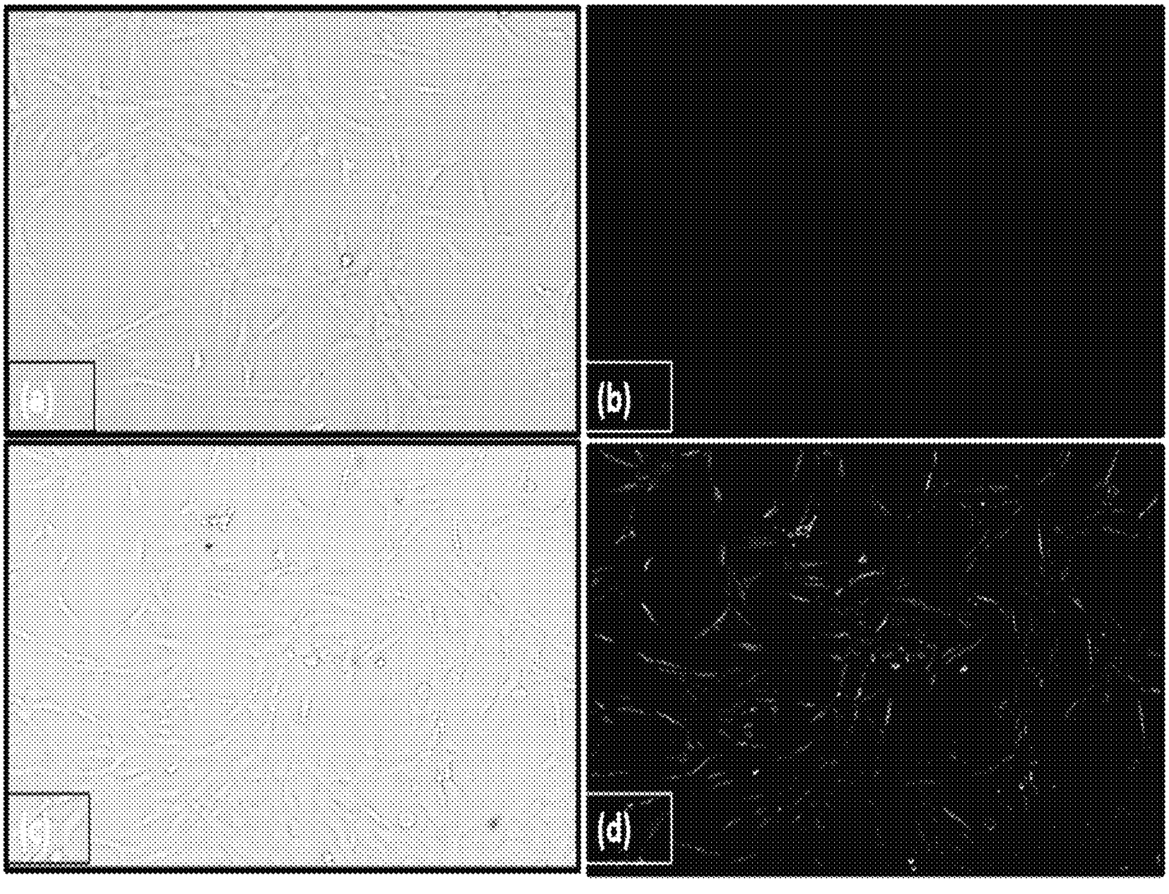

FIG. 19. (a) Untreated control HCEC cells (DIC mode), (b) control (FITC mode), (c) cumarine-6 labelled CHLF-NLCs treated cells (DIC mode), (d) cumarine-6 labelled CHLF-NLCs treated cells (FITC mode).

Figure 20:
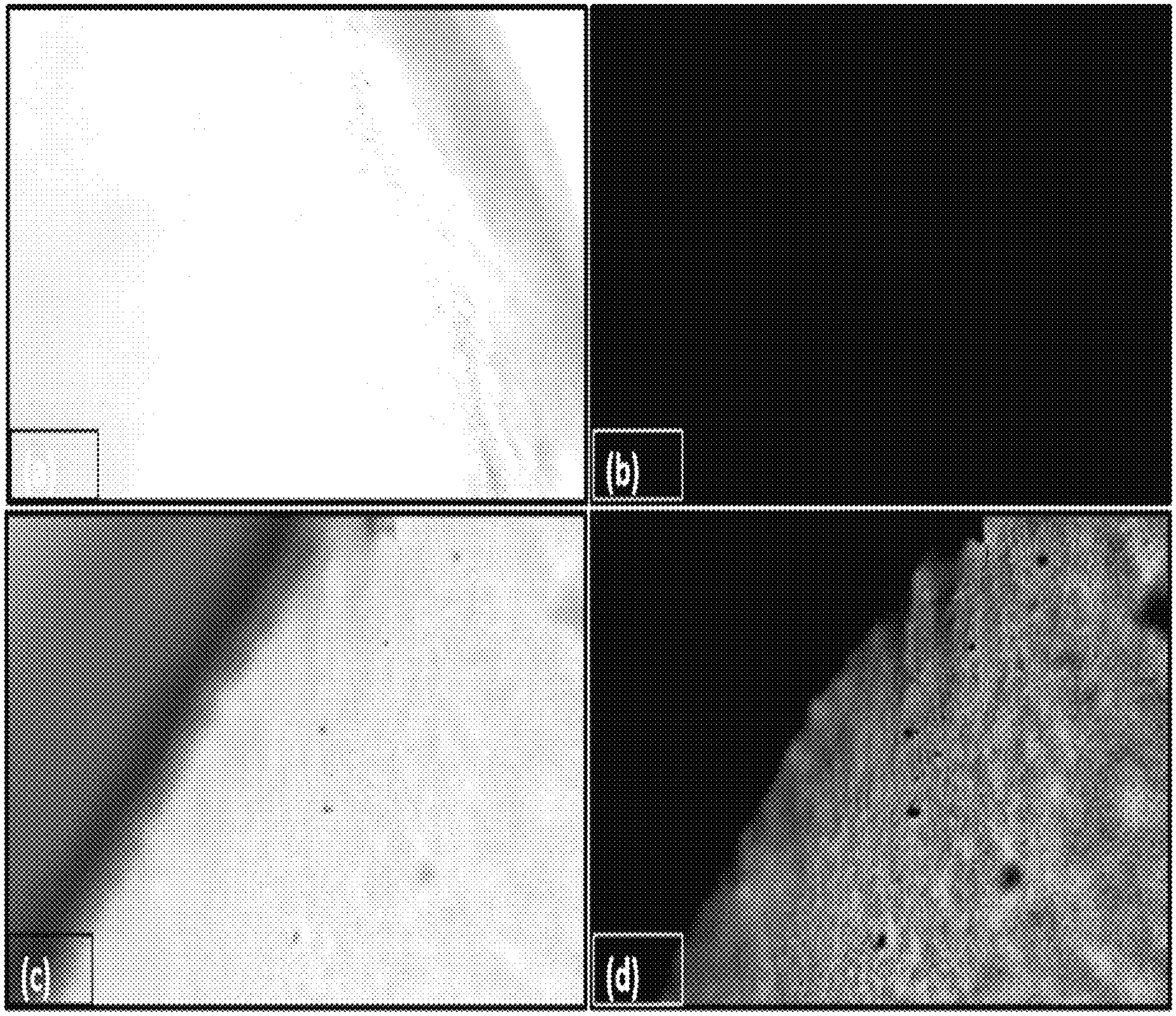

FIG. 20. (a) Untreated control cornea (DIC mode), (b) control (FITC mode), (c) cumarine-6 labelled CHLF-NLCs treated cornea (DIC mode), (d) cumarine-6 labelled CHLF-NLCs treated cornea (FITC mode).

Figure 21:
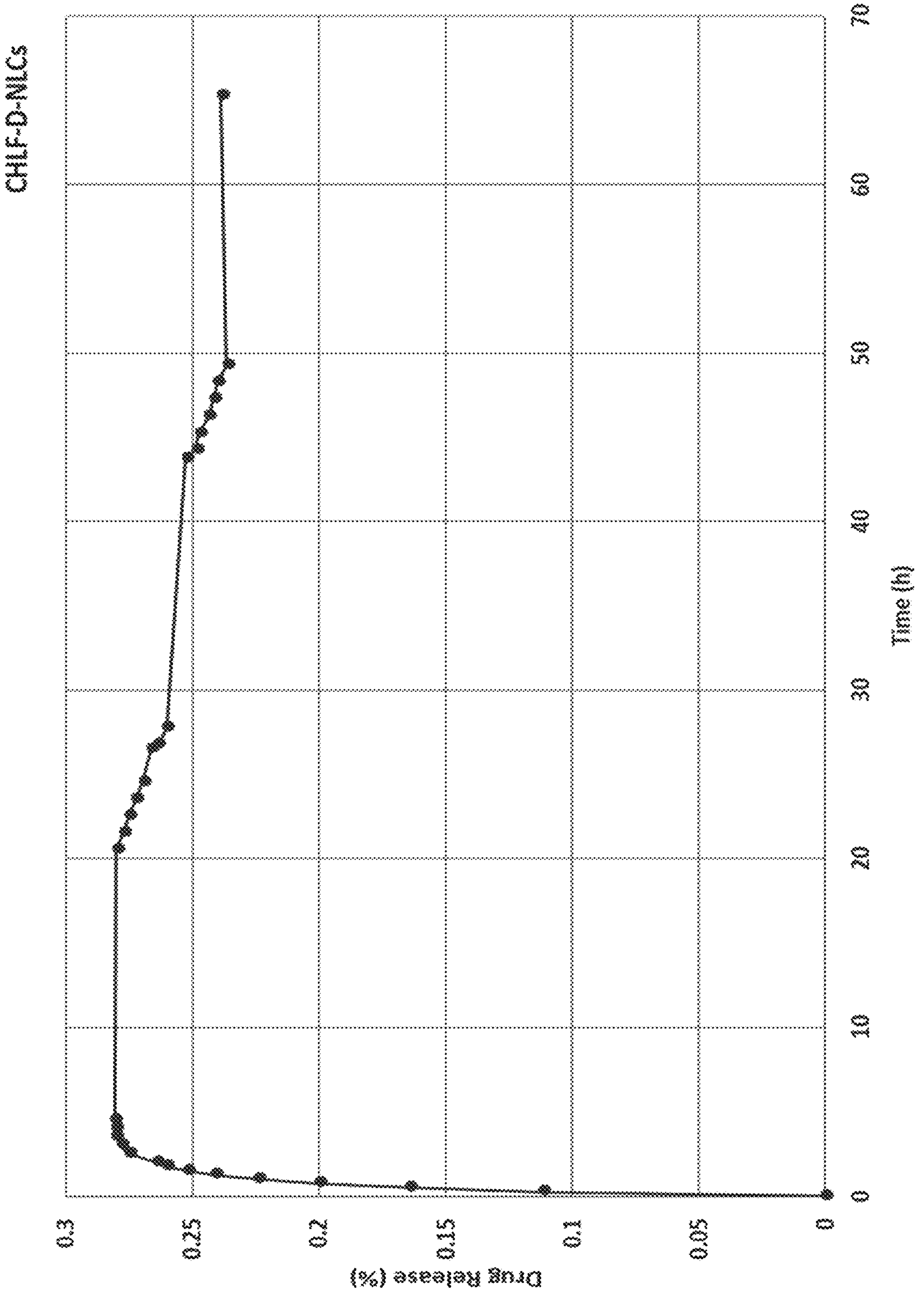

FIG. 21. Drug release study of pilot scale CHLF-D-NLCs.

Figure 22:
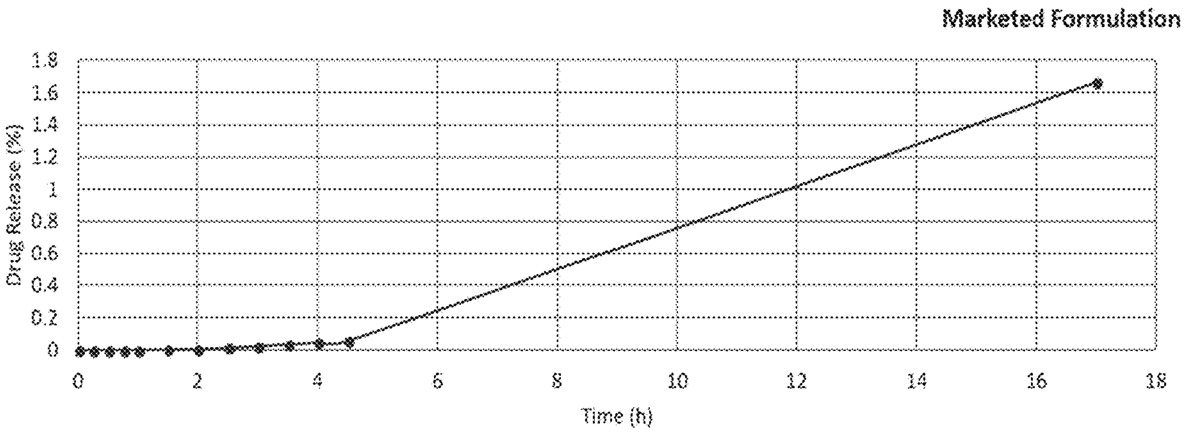
Figure 22:
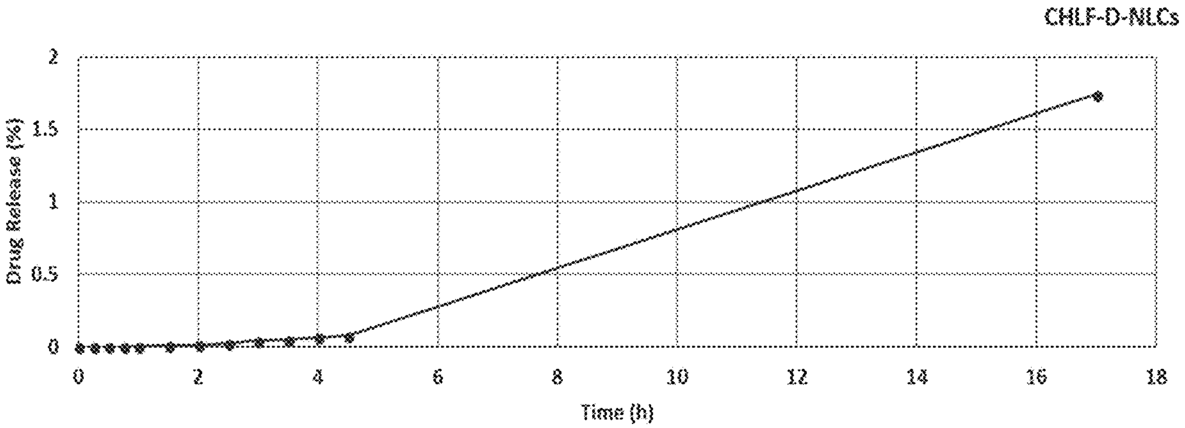

FIG. 22. Permeation study of marketed formulation and pilot scale CHLF-D-NLCs.

Figure 23:
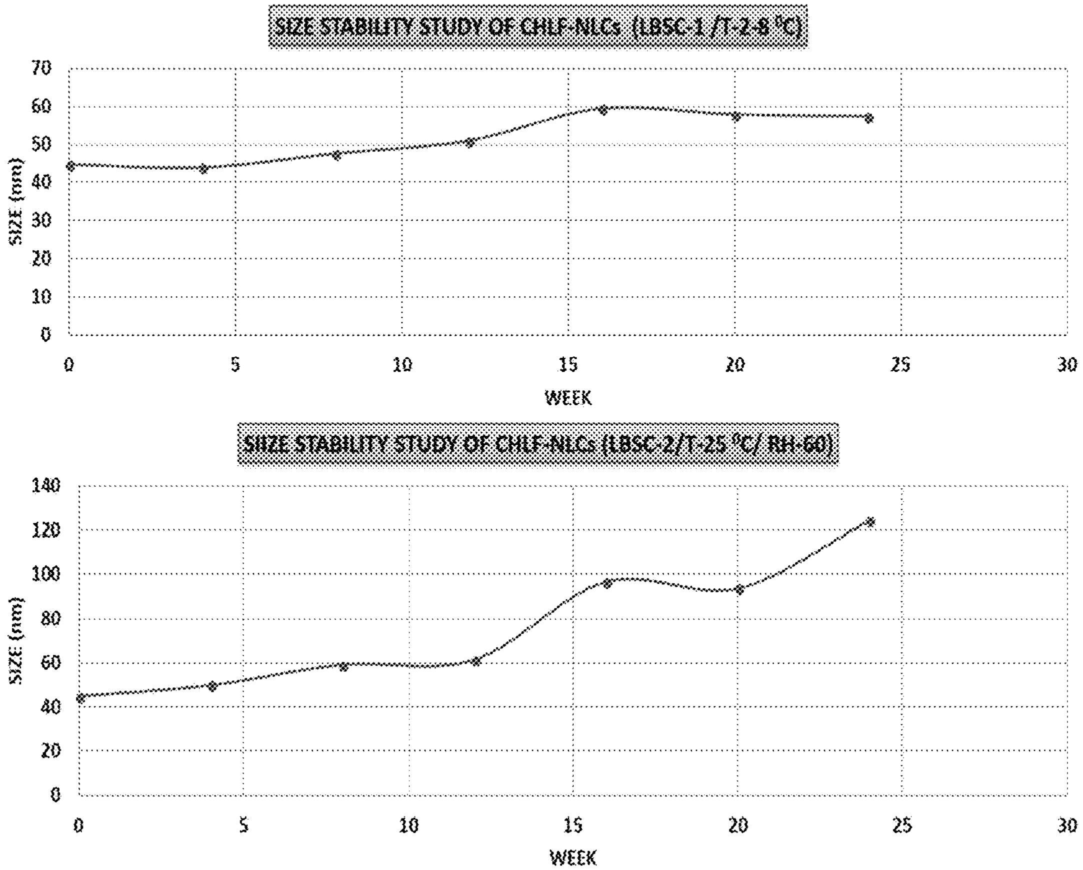

FIG. 23. Size stability study of lab scale samples.

Figure 24:
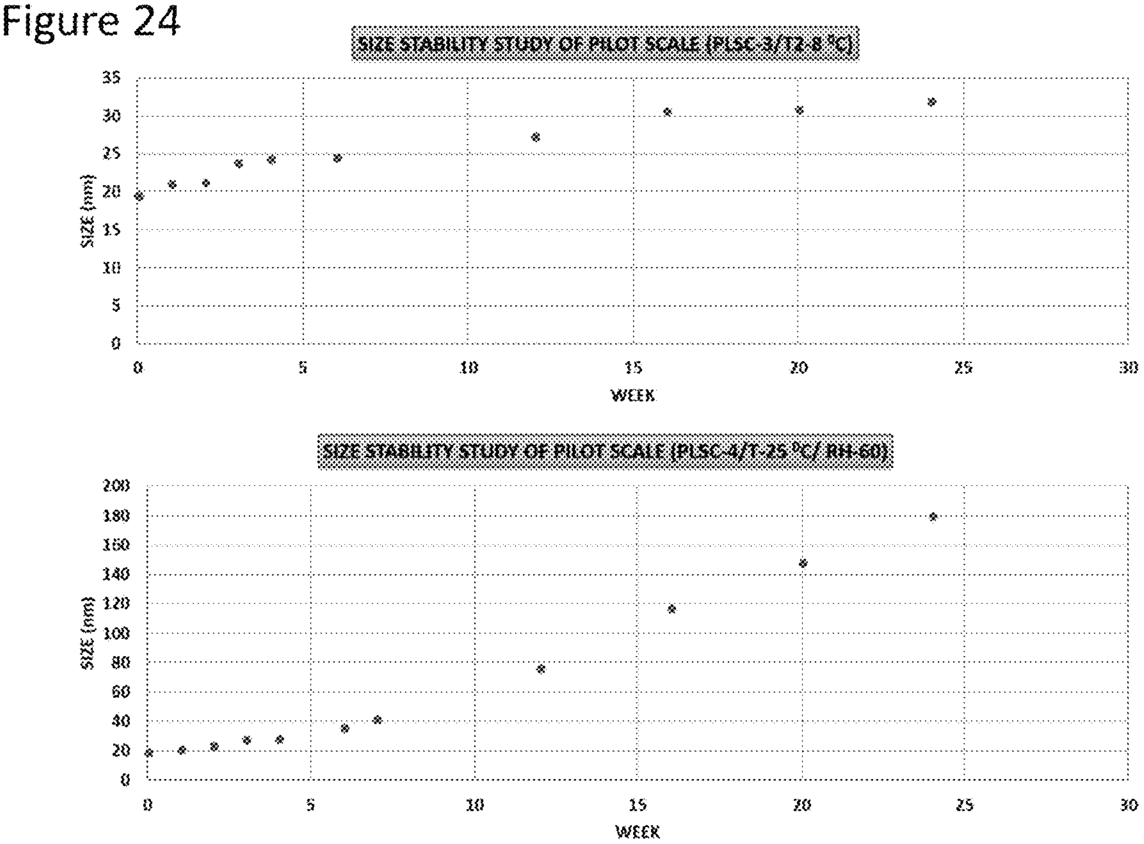

FIG. 24. Size stability study of Pilot scale samples.

Figure 25:
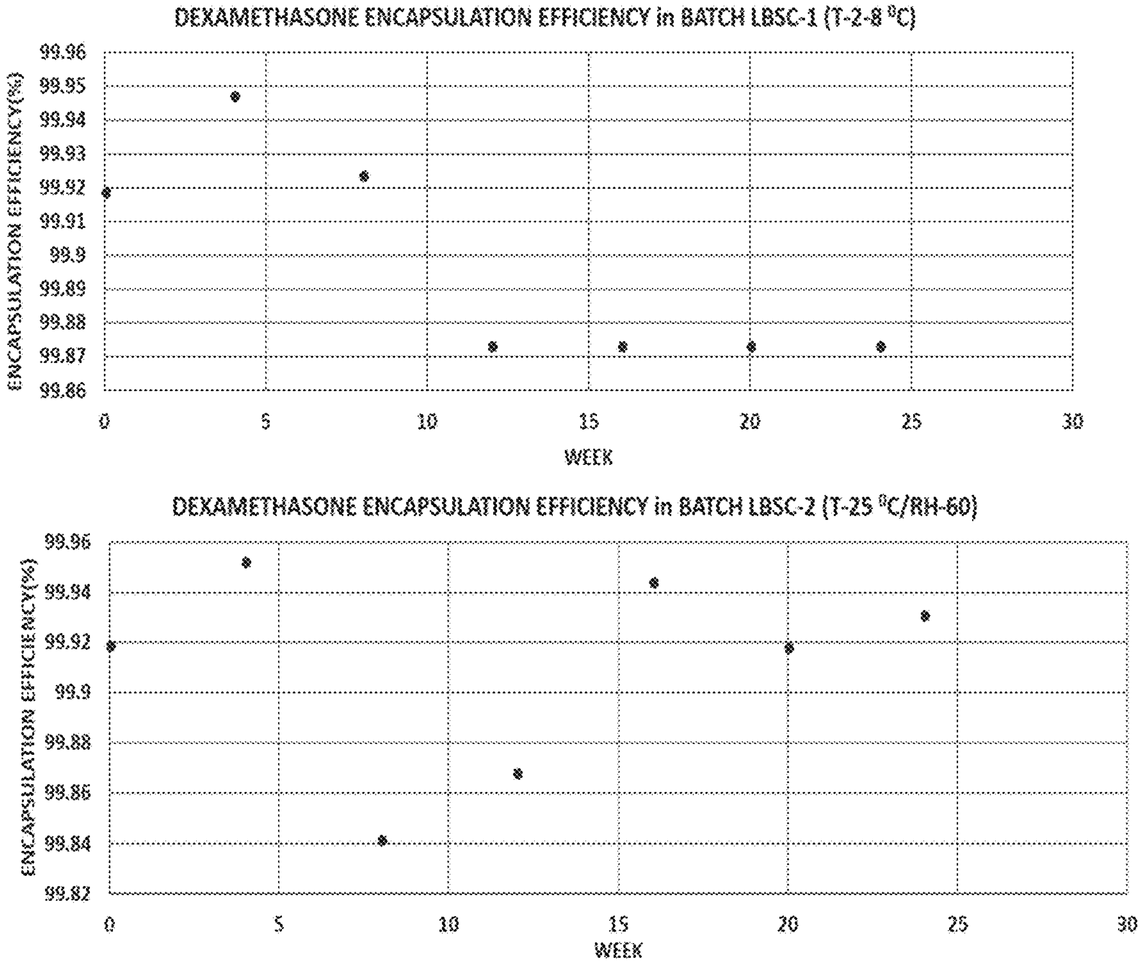

FIG. 25. Dexamethasone encapsulation efficiency stability study of Lab scale samples.

Figure 26:
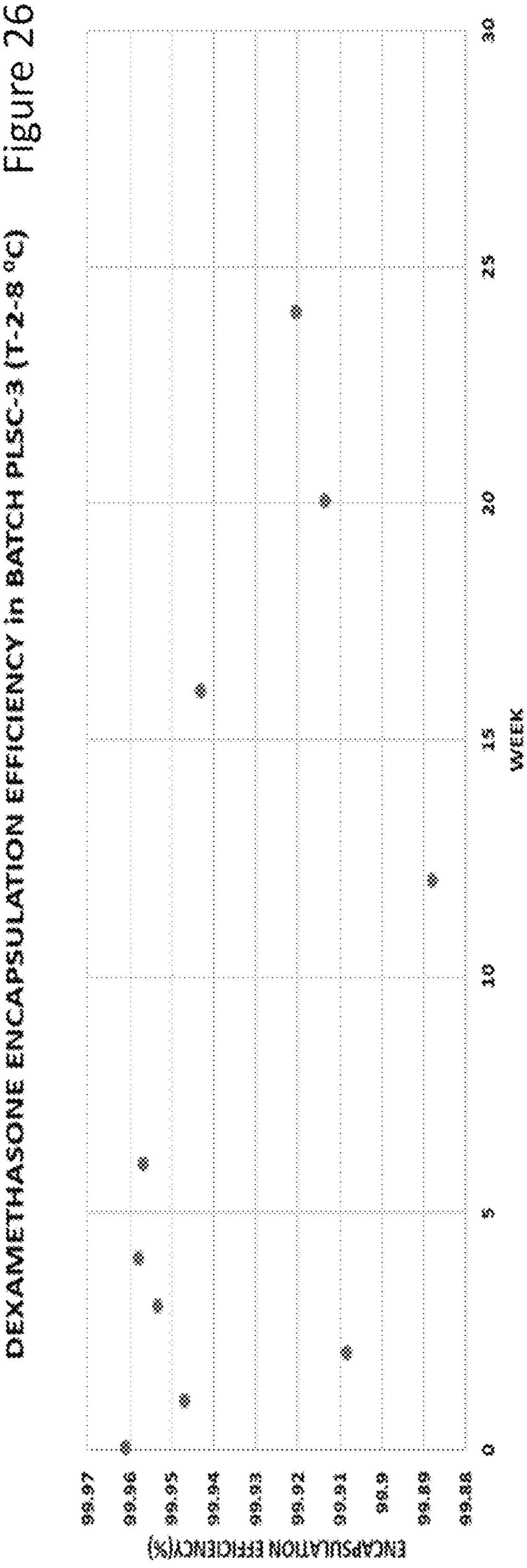
Figure 26:
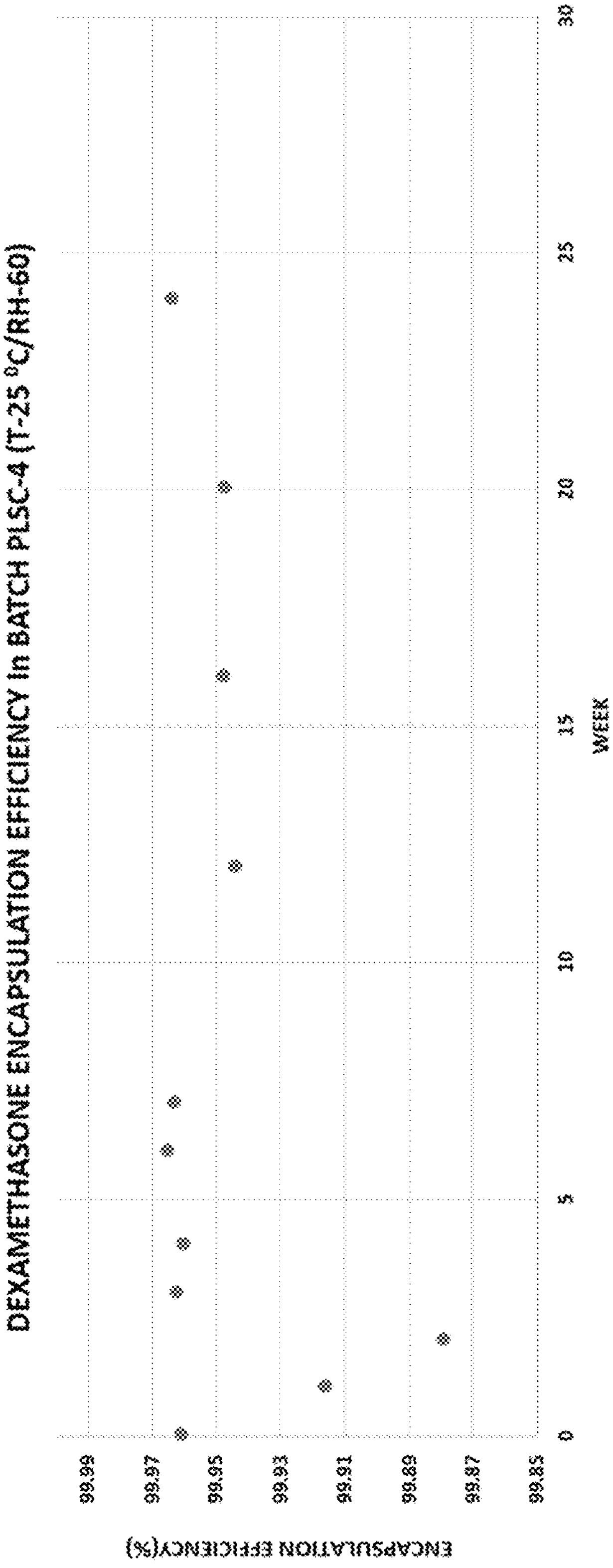

FIG. 26. Dexamethasone encapsulation efficiency stability study of Pilot scale samples.

Figure 27:
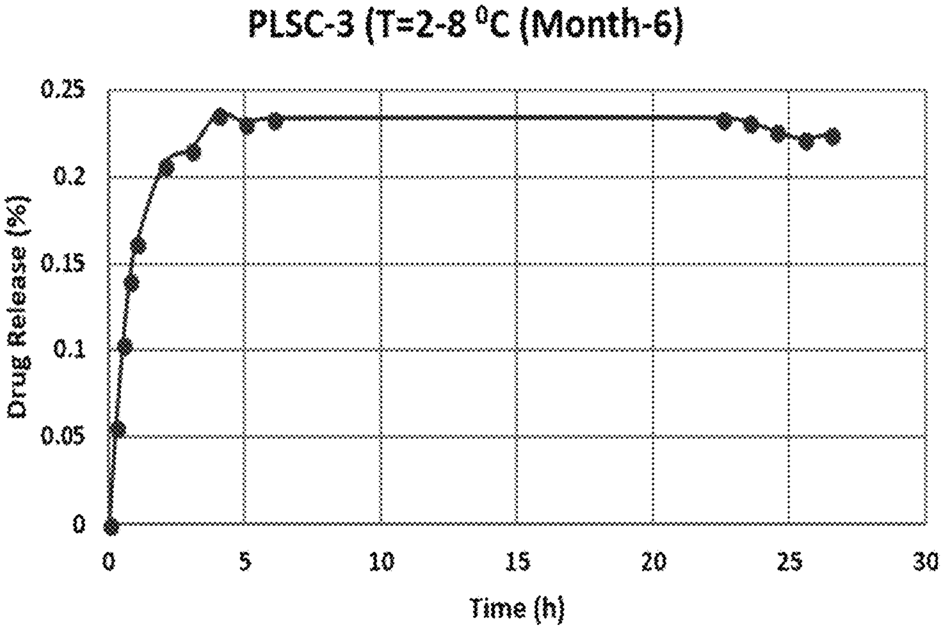

FIG. 27. Drug release study is performed for sample PLSC-3 after 6 months.

Figure 28:
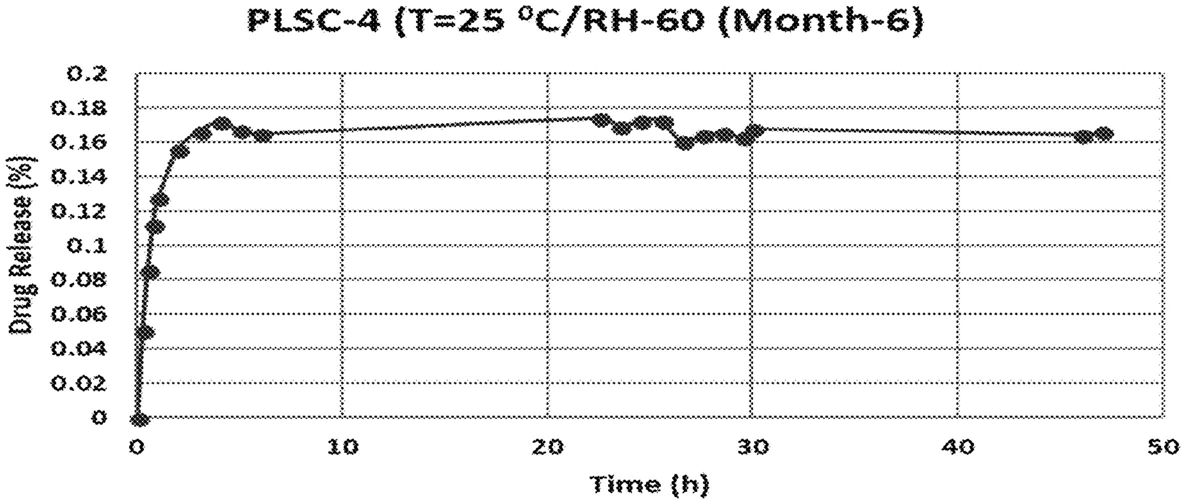

FIG. 28. Drug release study is performed for sample PLSC-4 after 6 months.

Figure 29:
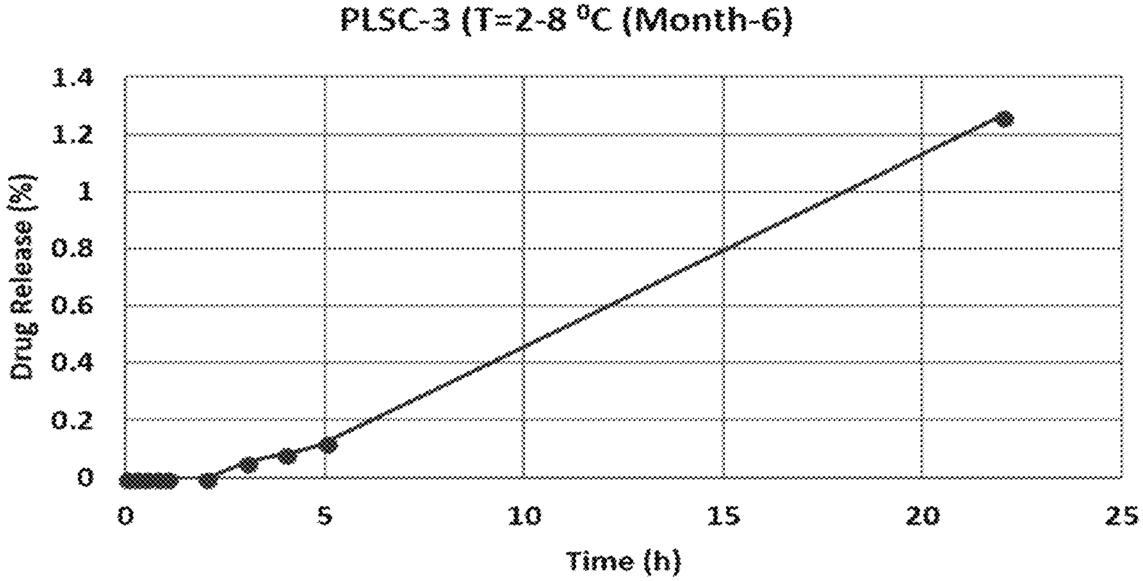

FIG. 29. Permeation study is performed for sample PLSC-3 after 6 months.

Figure 30:
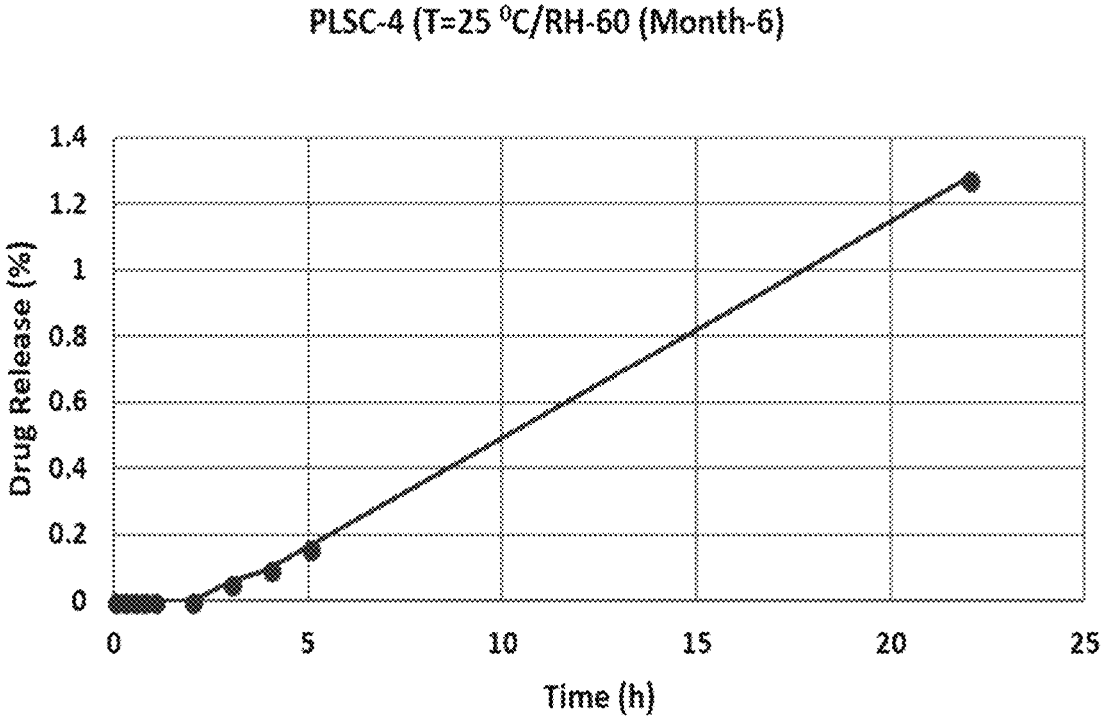

FIG. 30. Permeation study is performed for sample PLSC-4 after 6 months.

Figure 31:
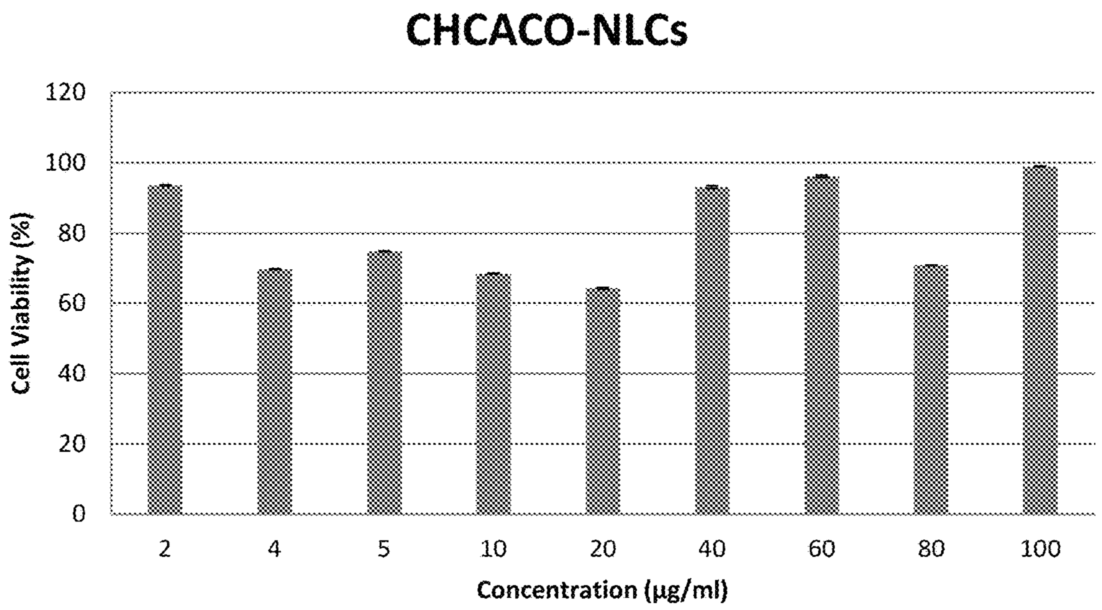

FIG. 31. Cytotoxicity study of CHCACO-NLCs with MTT assay.

Figure 32:
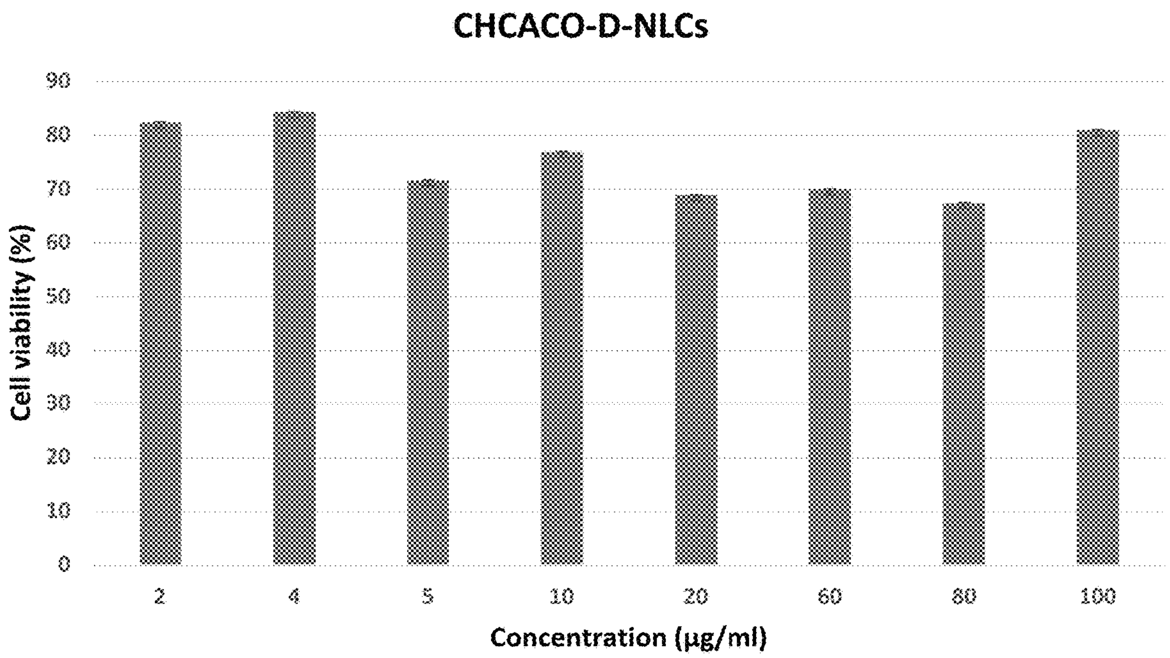

FIG. 32. Cytotoxicity study of CHCACO-D-NLCs (Drug loaded NLCs) with MTT assay.

Figure 33:
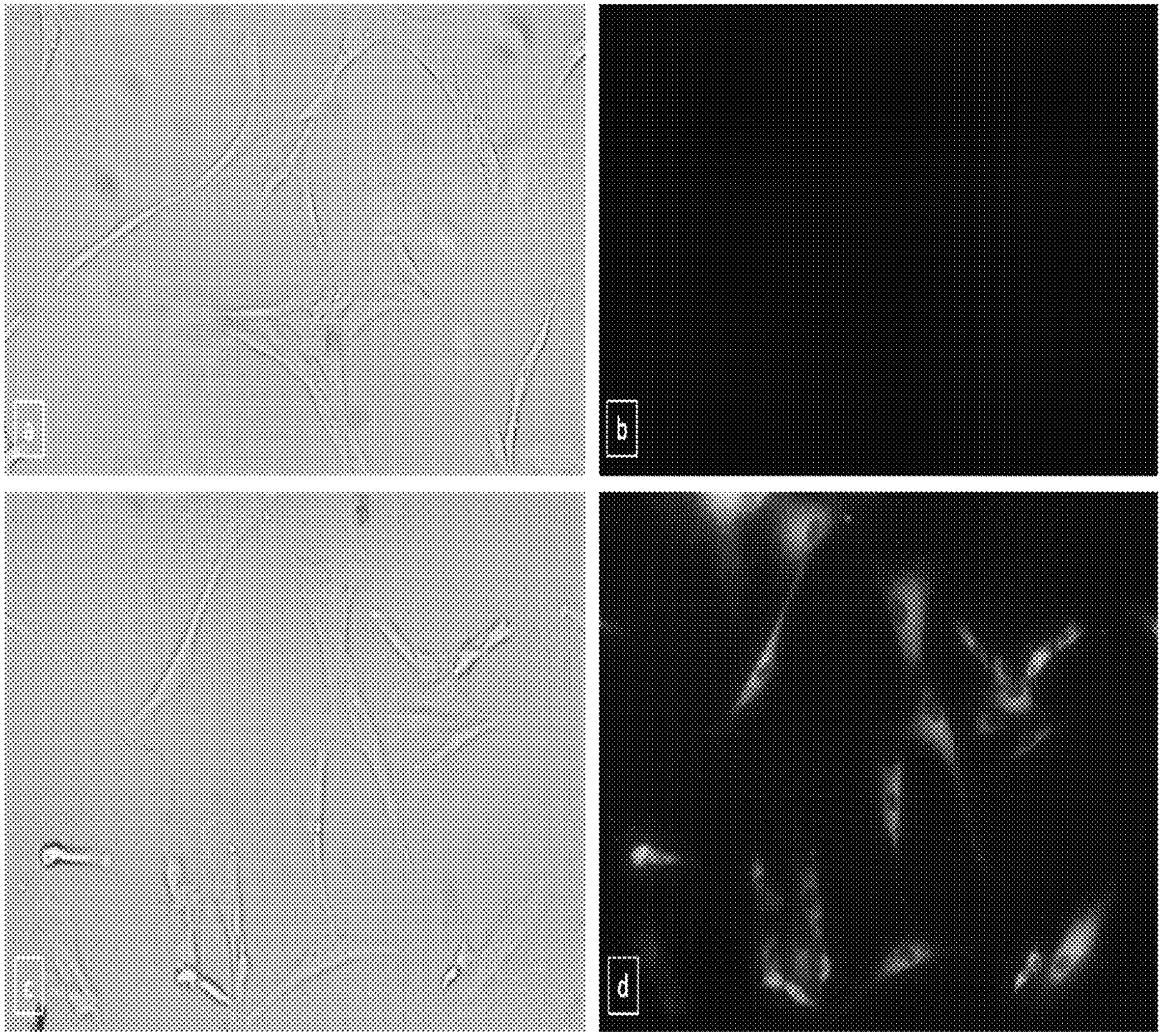

FIG. 33. Cellular uptake study of CHCACO-NLCs.

Figure 34:
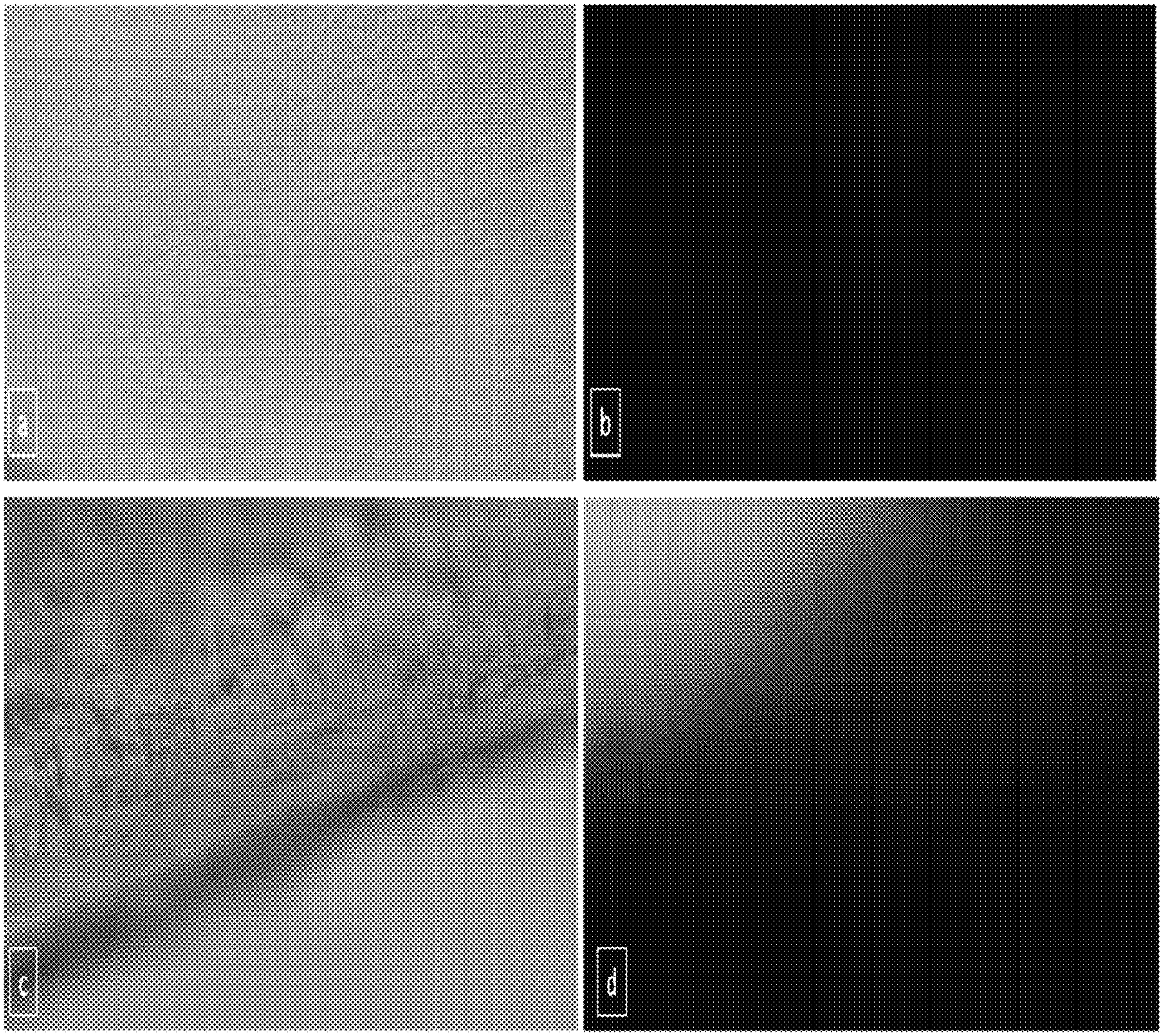

FIG. 34. Mucoadhesion study of CHCACO-NLCs.

Figure 35:
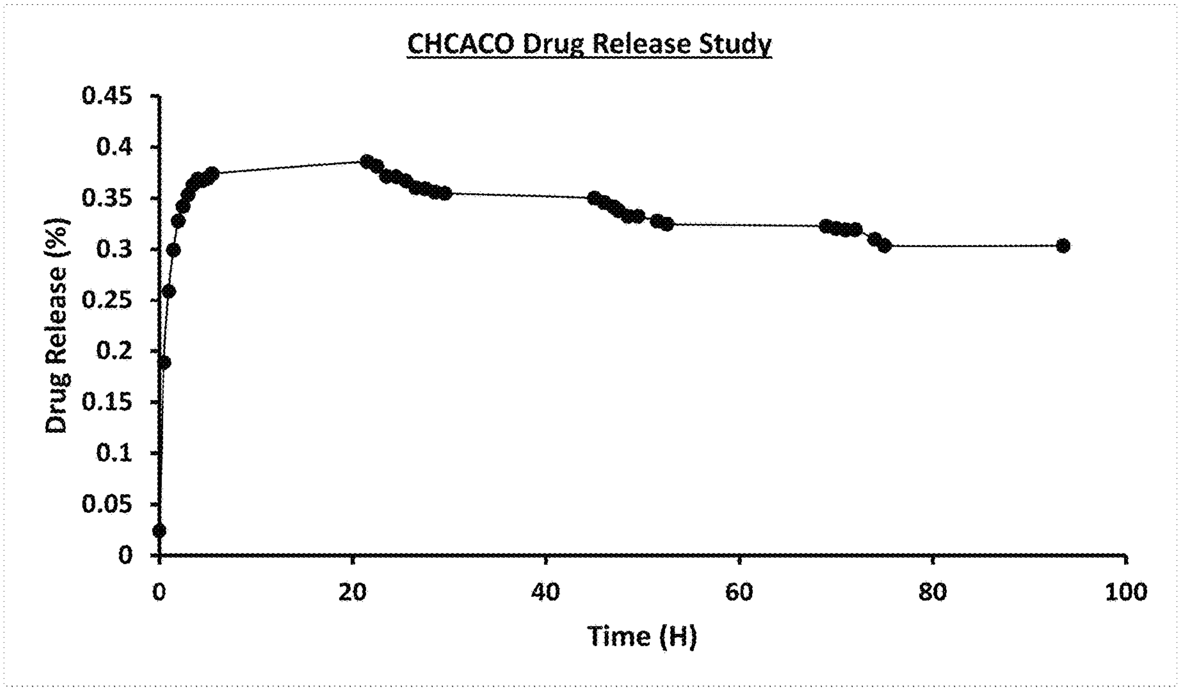

FIG. 35. Drug release study of CHCACO-D-NLCs, and

Figure 36:
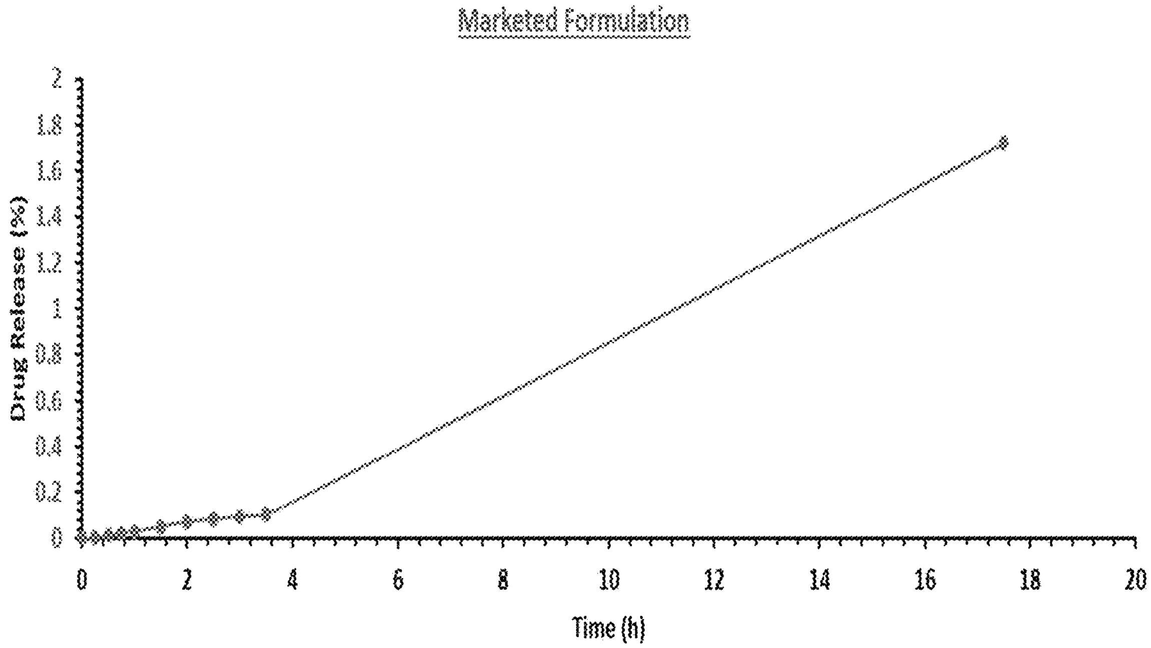
Figure 36:
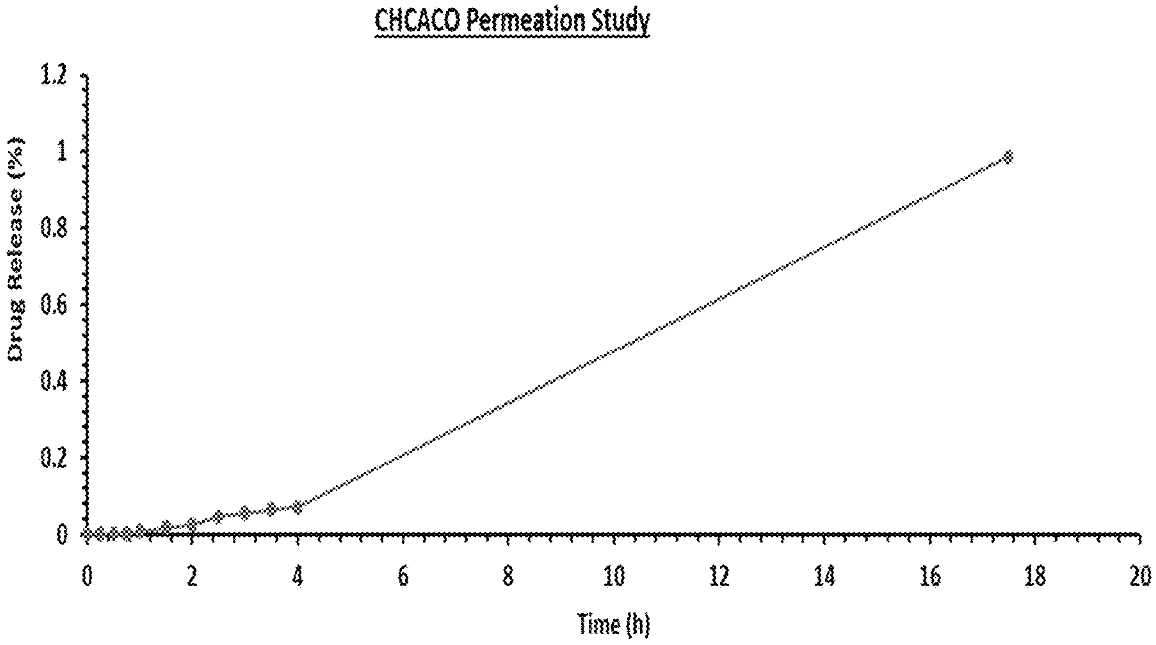

FIG. 36. Permeation study of CHCACO-D-NLCs.

EXAMPLE 1

Nanostructured Lipid Carriers (NLCs) of Cholesterol-Labrafac Lipophile® WL 1349 (CHLF)

Nanostructured lipid carriers (NLCs) of cholesterol-Labrafac Lipophile® WL 1349 (CHLF) lypophile have been designed, optimised, synthesised and characterized. The prepared cholesterol-Labrafac Lipophile® WL 1349 NLCs encapsulated anti-inflammatory corticosteroid drug dexamethasone (DX). The CHLF-NLCs are transported transcellularly to cornea. The Labrafac Lipophile® WL 1349 acts as a penetration enhancer and facilitates the release of the drug in the cytoplasm of corneal cells. The CHLF-NLCs were further studied for cytotoxicity, cellular internalisation, ex vivo mucoadhesion with cornea, controlled extended drug release and permeation. The present invention discloses technology for the synthesis of NLCs of CHLF, which can be used for the patients suffering from ophthalmic inflammatory conditions such as acute and chronic dry eye.

Cytotoxicity Assessment of the Prepared NLC.

The cytotoxicity of the NLC was carried out on Human Corneal Epithelium Cell (HCEC). The cells with the initial density of 10,000 cells/well were seeded in a 96-well plate and were then cultured for 24 h in DMEM medium containing 10% FBS. The cells were then treated with varying concentrations of NLC, and NLC treated cells were incubated in a humidified environment with 5% $CO_2$ at 37° C. for 4 h. After 4 h culture medium is replaced with the fresh medium, the cells were further maintained for another 20 h. After the specified time, MTT reagent (5 mg/mL) was added to each well, and the cells were incubated for another 4 h. The medium in each well was replaced with 200 μL of DMSO to dissolve the formazan crystals. The absorbance (O.D.) was recorded with a microplate reader. The cell viability was calculated by using the following equation:

$$\text{Cell viability (\%)} = [O.D.\ (\text{test})/O.D.\ (\text{control})] \times 100$$

Where O.D. (test) and O.D. (control) are the absorbance values of the cells cultured with and without NLC, respectively.

The cytotoxicity study showed that prepared CHLF-NLC is non-toxic. In particular, the experiment using a 1:30 ratio was performed to a concentration of 200 microgram/ml where it showed cell viability. In the 1:4 ratio the experiment was performed to a concentration of 100 microgram/ml and showed cell viability.

In Vitro Cellular Internalization of the NLCs were Examined with Fluorescence Microscopy.

The cellular uptake of FITC labelled NLC was further examined using fluorescent microscopy. The cells were seeded in confocal imaging dishes at a density of $5\times10^4$ cells per dish. The FITC labelled NLC were prepared and were exposed to the HCEC cells in serum free DMEM medium. After 4 h of incubation at 37° C., NLC treated serum free medium was removed and the cells were washed with without phenol red DMEM. Further 1 ml of without phenol red DMEM was added to the cells and the cellular uptake study was performed under fluorescent microscope. The data showed that the FITC labelled CHLF-NLC are internalised in the HCEC cells within 4 hours.

Mucoadhesion Study was Performed Ex Vivo with Pig Cornea and Examined Under Fluorescence Microscope.

The Mucoadhesion study of FITC labelled NLC on pig cornea was further examined using fluorescent microscopy. The pig cornea was excised and placed in the confocal imaging dishes containing without phenol red DMEM. The FITC labelled NLC were prepared and were exposed to the cornea in serum free DMEM medium. After 4 h of incubation at 37° C., NLC treated serum free medium was removed and the cornea was washed with without phenol red DMEM. Further, 1 ml of without phenol red DMEM was added to the cornea and the Mucoadhesion study on cornea was performed under fluorescent microscope.

The study showed that the CHLF-NLC are mucoadhesive, as the data showed that the NLC particles stick to the cornea.

Drug Release Study is Performed with Definite Concentration of Drug in CHLF-NLCs Over a Period of 18 Days.

The drug release study was performed over 18 days for CHLF-NLC (1:30), and was performed by dialysis membrane. 1 ml of the drug loaded CHLF-NLC was taken in the dialysis membrane with concentration of drug 1 mg/ml. The membrane was clipped and dipped into the phosphate buffered saline (PBS) of pH=7.4 and temperature was maintained at 37° C. The PBS was stirred with a magnetic bead. 1 ml of the PBS was collected after different time intervals and 1 ml of fresh PBS was added to maintain the volume of the PBS. The collected sample was analysed with HPLC.

The drug release data showed that the drug was released over time. In particular, the study was performed for the 1:30 ratio of CHLF-NLC for 18 days/381.2 h. In the case of the 1:4 ratio of CHLF-NLC, the study was performed for 81.5 hours.

Permeation Study is Explored with Cornea Over the Definite Interval of Time

The permeation study was performed ex-vivo with pig cornea. The excised cornea fit in the Franz diffusion cell. The donor chamber was filled with drug loaded CHLF-NLC (concentration of drug 1 mg/ml). In the acceptor chamber PBS of pH=7.4 was taken and stirred with a magnetic bead and the chamber was maintained at the temperature of 37° C. 1 ml of the PBS was collected at different time intervals and 1 ml of fresh PBS was added to maintain the volume of the PBS in the acceptor chamber. The collected sample was analysed with HPLC.

The permeation study showed that the drug is efficiently released through the cornea.

Size Measurement and Stability Study with Dynamic Light Scattering (DLS) (Table 1).

The synthesised NLCs have a size range from 100-500 nm.

TABLE 1

Size and zeta potential of CHLF NLCs with and without drug loading

| Sample | Dexamethasone (mg/ml) | Particle size (nm) | Zeta potential (mV) |
|---|---|---|---|
| CHLF | 0 | 285 | −25.6 |
| CHLF-D | 1 | 483 | −23.6 |

Zeta potential can be determined with instruments such as the MICROTRAC NANOWAVE II. Measurement of zeta-potential is also described in Salopek et al. (1992. Rudarsko-geolosko-naftni zbornik, Vo. 4, pp. 147-151, Zagreb), which provides the following guidelines of suspension stability depending on zeta-potential size:

| Assessment of stability | Zeta-Potential (mV) |
|---|---|
| Maximal agglomeration and precipitation | 0 . . . +3 |
| Region of strong agglomeration precipitation | +5 . . . −5 |
| Beginning of agglomeration | −10 . . . −15 |
| Beginning of peptization (disperging) | −16 . . . −30 |
| Medium stability | −31 . . . −40 |
| Good stability | −41 . . . −60 |
| Very good stability | −61 . . . −80 |
| Extremely good stability | −81 . . . −100 |

Cytotoxicity Assessment of the Prepared CHLF-NLC (1:4).

The cytotoxicity of the NLC was carried out on Human Corneal Epithelium Cells (HCEC). The cells with an initial density of 10,000 cells/well were seeded in a 96-well plate and were then cultured for 24 h in DMEM medium containing 10% FBS. The cells were then treated with varying concentrations of NLC, and NLC treated cells were incubated in a humidified environment with 5% $CO_2$ at 37° C. for 4 h. After 4 h the culture medium was replaced with fresh medium, the cells were further maintained for another 20 h. After the specified time, MTT reagent (5 mg/mL) was added to each well, and the cells were incubated for another 4 h. The medium in each well was replaced with 200 μL of DMSO to dissolve the formazan crystals. The absorbance (O.D.) was recorded with a microplate reader. The cell viability was calculated by using the following equation:

$$\text{Cell viability (\%)} = [O.D.\ \text{(test)}/O.D.\ \text{(control)}] \times 100$$

Where O.D. (test) and O.D. (control) are the absorbance values of the cells cultured with and without NLC, respectively The cytotoxicity study showed that prepared 1:4 ratio CHLF-NLC is non-toxic up to the concentration of 100 μg/ml.

In Vitro Cellular Internalization of the NLCs was Examined with Fluorescence Microscopy.

The cellular uptake of coumarin-6 labelled NLC was further examined using fluorescent microscopy. The cells were seeded in confocal imaging dishes at a density of $5\times10^4$ cells per dish. The coumarin-6 labelled NLC were prepared and were exposed to the HCEC cells in serum free DMEM medium. After 4 h of incubation at 37° C., NLC treated serum free medium was removed and the cells were washed with without phenol red DMEM. Further 1 ml of without phenol red DMEM was added to the cells and the cellular uptake study was performed under fluorescent microscope. The data showed that the coumarin-6 labelled NLC are internalised in the HCEC cells within 4 h.

Mucoadhesion Study was Performed Ex Vivo with Pig Cornea and Examined Under Fluorescence Microscope.

The Mucoadhesion study of coumarin-6 labelled NLC on pig cornea was further examined using fluorescent microscopy. The pig cornea was excised and placed in the confocal imaging dishes containing without phenol red DMEM. The coumarin-6 labelled NLC were prepared and were exposed to the cornea in serum free DMEM medium. After 4 h of incubation at 37° C., NLC treated serum free medium was removed and the cornea was washed with without phenol red DMEM. Further 1 ml of without phenol red DMEM was added to the cornea and cellular mucoadhesion study was performed under fluorescent microscope.

The study showed that the CHLF-NLC (1:4 ratio) are mucoadhesive, as the data showed that the NLC particles stick to the cornea.

Drug Release Study is Performed with Drug Encapsulated CHLF-NLCs with the Drug Concentration 1 mg/ml Over the Time of 81.5 Hr.

The drug release study was performed by dialysis membrane. 1 ml of the drug loaded CHLF-NLC was taken in the dialysis membrane with a drug concentration of 1 mg/ml.

The membrane was clipped and dipped into the phosphate buffered saline (PBS) of pH=7.4 and temperature was maintained at 37° C. The PBS was stirred with a magnetic bead. 1 ml of the PBS was collected at different time intervals and 1 ml of fresh PBS was added to maintain the volume of the PBS. The collected sample was analysed with the HPLC.

The drug release data showed that the drug is released over the time of 81.5 Hr.

Permeation Study is Explored with Cornea Over the Definite Interval of Time.

The permeation study was performed ex-vivo with pig cornea. The excised cornea fit in the Franz diffusion cell. The donor chamber was filled with drug loaded CHLF-NLC (concentration of drug 1 mg/ml). In the acceptor chamber PBS of pH=7.4 was taken and stirred with a magnetic bead and the chamber was maintained at the temperature of 37° C. 1 ml of the PBS was collected after different time intervals and 1 ml of fresh PBS was added to maintain the volume of the PBS in the acceptor chamber. The collected sample was analysed with HPLC.

The permeation study showed that the drug is efficiently released through the cornea.

Size Measurement and Stability Study with Dynamic Light Scattering (DLS) (Table 1).

The synthesised NLCs have size range from 100-500 nm.

TABLE 2

Size and zeta potential of CHLF NLCs with and without drug loading

| SAMPLE NAME | DRUG CONTENT (mg/ml) | PARTICLE SIZE (nm) | ZETA POTENTIAL (mV) |
|---|---|---|---|
| CHLF 1:4 | 0 | 336 | −10.2 |
| CHLF-D 1:4 | 1 | 153.4 | −12.2 |

CHLF-NLC and CHLF-D-NLC are characterised by DLS. It has been observed that CHLF-NLC have a particle size of 336 nm and zeta potential of −10.2 mV and CHLF-D-NLC have a particle size of 153.4 nm and zeta potential of −12.2 nm.

Results & Discussion

All studies showed a positive result for the synthesised NLCs indicating that these NLCs are a viable option for conventional eye drops for dry eye treatment. In the present invention of drug encapsulated NLCs, the drug is released from the carrier system and controlled by a diffusion and hydration. The drug release from the carrier can also be controlled by ionic interaction between the lipid and drug. In this invention, the drug molecule is present in the Labrafac Lipophile® WL 1349, which is a medium chain triglyceride. The Labrafac Lipophile® WL 1349 is entrapped in cholesterol. The NLCs are transported transcellularly to cornea. The Labrafac Lipophile® WL 1349 acts as penetration enhancer and facilitates the release of drug in the cytoplasm of corneal cells.

The CHLF-NLC is mucoadhesive, as shown in the ex vivo experimental result. The NLC will show better bioavailability, because the ex vivo study showed that CHLF-NLC is mucoadhesive and the in vitro cellular uptake study showed that CHLF-NLC are internalised in the human corneal epithelium cell (HCEC).

As cell membrane consists of lipid bilayer including cholesterol, better diffusion of NLC through the cell membrane is expected. The liquid lipid, e.g. Labrafac Lipophile® WL 1349, acts as a penetration enhancer and facilitates the release of the drug in the cytoplasm of corneal cells. In particular, the eye surface is covered with a mucus layer. The mucus glycoproteins on the surface of eye have various subdomains rich in specific amino acids. These amino acids are positively charged due to the amino group. Mucus glycoprotein is a protein that contains oligosaccharide chains covalently attached to polypeptide side chain. Peptides are short chain amino acids (e.g. cysteine, lysine), which are linked by amide bond. These amino acids are positively charged due to the amino group.

The developed drug encapsulated NLCs are negatively charged and can interact with the mucus glycoproteins. This interaction leads to the enhanced residence time of NLCs and expected to enhance the drug bioavailability.

NLCs have higher tolerability, permeability, sustained delivery, and storage stability.

a) Tolerability: NLCs are expected to show good tolerability as the cholesterol component of NLCs is already there in the cell membrane, so it is expected to show good tolerability. The Labrafac Lipophile® WL 1349 is already used in skin cosmetics, so it is expected to show good tolerability.

b) Permeability: Regarding permeability, the permeation study data shows that NLCs have good permeability.

c) Sustained delivery: Drug release data shows that initially an increase in drug release is obtained which becomes nearly sustainable with time, with only mild variation. The NLCs have shown efficient controlled drug release over the period of 18 days for CHLF-NLC ratio 1:30 ratio and 81.5 hr for CHLF-NLC ratio 1:4.

d) Storage stability: From the zeta potential study it showed that the prepared NLCs are stable in suspension.

The present technology shields the encapsulated drug from the physiological barrier of the eye and facilitates the drug release at the targeted site. This technology will provide the therapeutic enhancement with the properties of enhanced biocompatibility, mucoadhesion, bioavailability, less drainage, increased residence time, reduced dosage frequency, and provides an efficient carrier for drug delivery.

Due to these properties, the present invention is highly efficient for use as an eye drop based formulation. Due to the mucoadhesion property of the NLCs, the invention will have enhanced retention on the corneal surface with controlled released of drug over a prolonged duration. These NLCs can reduce the dosage frequency. The ex vivo permeation study also shows efficient release of drug. The studies have shown that present technology efficiently overcomes the problems which have been observed in already marketed formulations.

EXAMPLE 2

Development of Dexamethasone Loaded Cholesterol-Labrafac Nanostructed Lipid Carrier (CHLF-D-NLCs)

Pilot Scale Sample Preparation by High Pressure Homogeniser

Cholesterol-labrafac of ratios 1:4 is selected, which was observed to be stable for the lab scale. The Cholesterol-labrafac ratio 1:4 is taken in a beaker 1 to this added acetone and ethanol in equal ratio. In a beaker 2, 1% tween 80 prepared in aqueous medium is taken. Both the beakers stirred and heated in a water bath at equal temperature (60-65° C.) for mixing and dissolving the component. After few min, when beaker 1 solvent is almost evaporated, hot 1% tween 80 is added to it, which results in white emulsion formation. The emulsion is stirred at the same temperature for another 5 mins. After 5 mins emulsion sample is cycled through High Pressure Homogeniser for 5 min, which result in the formation of the CHLF-NLCs.

Preparation and Characterisation Of Dexamethasone Loaded Cholesterol-Labrafac Nanostructed Lipid Carrier (CHLF-D-NLCs)

Cholesterol-labrafac of ratios 1:4, dexamethasone 1 mg/ml (0.1% w/v) is taken in a beaker 1 to this added acetone and ethanol in equal ratio. In a beaker 2, 1% tween 80 prepared in aqueous medium is taken. Both the beakers stirred and heated in a water bath at equal temperature (60-65° C.) for mixing and dissolving the component. After few min, when beaker 1 solvent is almost evaporated, hot 1% tween 80 is added to it, which results in white emulsion formation. The emulsion is stirred at the same temperature for another 5 mins. After 5 mins emulsion sample is cycled through High Pressure Homogeniser for 5 min, which result in the formation of the CHLF-D-D-NLCs. The synthesised formulation is centrifuged and 0.01% of benzalkonium chloride is added to it. Further, formulation is sterilised by filtration through 0.2μ filter. The CHLF-D-NLCs is characterised by DLS.

Particle size measurement and zeta potential measurement: The particle size and zeta potential of the synthesised pilot scale sample is determined by DLS. The size and zeta potential of CHLF-NLCs is given in Table 3.

| SAMPLE NAME (Ratio) | DRUG CONTENT (mg/ml) | PARTICLE SIZE (nm) | ZETA POTENTIAL (mV) |
|---|---|---|---|
| CHLF-D-NLCs (1:4) | 1 | 20.64 | −7.1 |
| CHLF-D-PILOT SCALE STERLISED | 1 | 19.51 | 9.8 |

Encapsulation Efficiency of Dexamethasone Loaded CHLF-D-NLCs

Entrapment efficiency of dexamethasone entrapped in CHLF-NLC is determined by HPLC. For this 1 μl of CHLF-D-NLCs is added to the 999 μl of mobile phase—Phosphate Buffer (pH=3) and acetonitrile (ACN) in ratio 50:50. From the obtained area, the unknown concentration of the drug is determined by calibration curve and entrapment efficiency is calculated by the given formula $$\text{Encapsulation Efficiency (\%)} = \frac{\begin{array}{c}\text{(Drug Loaded} - \\ \text{free untrapped drug)}\end{array}}{\text{Drug Loaded}} * 100$$

It has been observed that the encapsulation efficiency (%) of CHLF-D-PILOT SCALE STERLISED formulation is 99.9%.

Experimental Study Performed with Pilot Scale Sample CHLF-NLCs Cytotoxicity Assessment of the Prepared CHLF-NLC The cytotoxicity of the pilot scale CHLF-D-NLC was carried out on Human Corneal Epithelium Cell (HCEC). The cells with the initial density of 10,000 cells/well were seeded in a 96-well plate and were then cultured for 24 h in DMEM medium containing 10% FBS. The cells were then treated with varying concentrations of CHLF-D-NLC, and CHLF-D-NLC treated cells were incubated in a humidified environment with 5% $CO_2$ at 37° C. for 4 h. After 4 h culture medium is replaced with the fresh medium, the cells were further maintained for another 20 h. After the specified time, MTT reagent was added to each well, and the cells were incubated for another 4 h. The medium in each well was replaced with 200 μl of DMSO to dissolve the formazan crystals. The absorbance (O.D.) was recorded with a microplate reader. The cell viability was calculated by using the following equation:

$$\text{Cell viability (\%)} = \left[\frac{O.D.\text{ (test)}}{O.D.\text{ (control)}}\right] * 100$$

Where O.D. (test) and O.D. (control) are the absorbance values of the cells cultured with and without NLC, respectively. The cytotoxicity study showed that prepared 1:4 ratio CHLF-D-NLC is non-toxic up to the given concentration FIG. 18.

Cellular Uptake Study

In vitro cellular uptake of coumarin-6 labelled CHLF-D-NLC was further examined using fluorescent microscopy. The cells were seeded in confocal imaging dishes at a density of $5\times10^4$ cells per dish. The coumarin-6 labelled CHLF-D-NLC were prepared and were exposed to the HCEC cells in medium. After 4 h of incubation at 37° C., CHLF-D-NLC treated medium is removed and the cells are washed. Further cellular uptake study is performed under fluorescent microscope. The data showed that the NLCs are internalised into the cells and coumarin-6, which is encapsulated in CHLF-D-NLCs is successfully released in the cytoplasm of the HCEC cells. Indicating that dexamethasone encapsulated in CHLF-D-NLCs will be released within the HCEC cells (FIG. 19).

Mucoadhesion Study

Mucoadhesion study was performed ex vivo with pig cornea. The mucoadhesion study of coumarin-6 labelled CHLF-NLC on pig cornea was further examined using fluorescent microscopy. The pig cornea is excised and placed in the confocal imaging dishes containing medium. The coumarin-6 labelled CHLF-NLC were prepared and were exposed to the cornea in medium. After 4 h of incubation at 37° C., CHLF-NLC treated medium is removed and the cornea is washed. Further mucoadhesion study is performed under fluorescent microscope. The mucoadhesion study showed that the CHLF-NLCs are mucoadhesive. As the CHLF-NLCs particles stick to the cornea (FIG. 20).

Drug Release Study

Drug release study is performed with drug encapsulated CHLF-NLCs with the drug concentration 1 mg/ml over the time of 65.25 h. The drug release study is performed by dialysis membrane. 1 ml of the drug loaded CHLF-NLC is taken in the dialysis membrane with concentration of drug 1 mg/ml. The membrane is clipped and dipped into the phosphate buffer saline (PBS) of pH=7.4 and temperature is maintained at 37° C. The PBS is stirred with magnetic bead. The 1 ml of the PBS is collected after different time interval and 1 ml of fresh PBS is added to maintain the volume of the PBS. The collected sample is analysed with the HPLC. The drug release data showed that drug is released over the time of 65.25 h (FIG. 21).

Permeation Study

The permeation study is performed ex-vivo with pig cornea. The excised cornea fit in the Franz diffusion cell. The donor chamber is filled with drug loaded CHLF-NLC (concentration of drug 1 mg/ml). In the acceptor chamber PBS of pH=7.4 is taken and stirred with magnetic bead and the chamber is maintained at the temperature of 37° C. The 1 ml of the PBS is collected after different time interval and 1 ml of fresh PBS is added to maintain the volume of the PBS in acceptor chamber. The collected sample is analysed with the HPLC. For the reference marketed formulation Maxidex is used for permeation. It has been observed that drug release percentage of the CHLF-D-NLCs is nearer to the value of marketed formulation. The study showed that dexamethasone is efficiently permeated through the cornea (FIG. 22).

Sterilisation of CHLF-D-NLCs Lab Scale and Pilot Scale Samples:

Lab scale and pilot scale samples are treated with benzalkonium chloride (BAK) (0.01% w/v). The BAK treated samples are filtered through 0.2 micron filter. The particle size and zeta potential of sterilised lab scale and pilot scale sample is determined with DLS. The study was carried out with lab scale and pilot scale samples.

Stability Study of CHLF-D-NLCs Lab Scale and Pilot Scale Samples

Stability study of sterilised lab scale and pilot scale sample is performed by Q1 Scientific Company for the period of 6 months. The analysis performed for the stability study sample is mainly size analysis by DLS to check the stability of size of CHLF-D-NLCs and drug encapsulation efficiency (%) analysis by HPLC to analyse the stability of encapsulation efficiency of CHLF-D-NLCs. For stability study four batches of samples (2 Batches for Lab Scale Sample (LBSC) and 2 Batches of pilot Scale Sample (PLSC)) are prepared, which are studied under two different temperature conditions. The stability study for all the four batches is performed for six months. After completion of 6 months, drug release and permeation study are performed for 6 months sample. Till the period of one-month pilot scale batch of samples are analysed weekly and after one month it has been analysed monthly. Lab scale samples are analysed monthly. The detail of the batches and their respective storage condition is given in Table 4.

| BATCH NAME | STORAGE CONDITION |
|---|---|
| LBSC-1 | 2-8° C. |
| LBSC-2 | 25° C./Relative Humidity (RH) 60 |
| PLSC-3 | 2-8° C. |
| PLSC-4 | 25° C./Relative Humidity (RH) 60 |

Stability Study Data Analysis Results

Data demonstrating the stability of the CHLF-NLC particles is presented in FIGS. 23-26.

Drug Release Study of 6-Month Sample

Data demonstrating the drug release from samples PLSC-3 and PLSC-4 are presented in FIGS. 27 and 28.

Permeation Study of 6-Month Sample

Data demonstrating the permeation of samples PLSC-3 and PLSC-4 are presented in FIGS. 29 and 30.

EXAMPLE 3

Synthesis of Dexamethasone Encapsulated Cholesterol-Coconut Oil-Castor Oil Based Nanostructured Lipid Career (CHCACO-NLCs) For Dry Eye Treatment This project is based on dexamethasone encapsulated in cholesterol-castor oil-coconut oil based nanostructured lipid carriers (CHCACO-NLCs). This technology showed the advantageous release of hydrophilic drug over the period of time.

This project was developed to treat acute and chronic dry eye with synthesised CHCACO-NLCs based eye drop. These NLCs is a viable option to replace conventional ointment, gels, eye drop. This material can lead to reduced dosage frequency and enhanced therapeutic output. The dexamethasone encapsulated CHCACO-NLCs were synthesised and characterised.

The NLCs particle size is determined with DLS instrument, where the particle size is in the range of 5-500 nm.

The cytotoxicity of the CHCACO-NLCs is determined with MTT assay.

In vitro cellular internalization of the CHCACO-NLCs was examined with fluorescence Microscopy.

The mucoadhesion study of CHCACO-NLCs is performed ex vivo with pig cornea and examined under fluorescence microscope.

The drug release study is performed with definite concentration of dexamethasone in CHCACO-NLCs over the period of time.

The permeation study is explored with cornea over the definite interval of time.

All studies showed positive results for the synthesised CHCACO-NLCs and indicate that these CHCACO-NLCs are viable option for conventional eye drop for dry eye treatment.

Optimisation of Cholesterol-Coconut Oil-Castor Oil Based Nanostructured Lipid Carrier In the optimization steps samples of different ratio have been synthesised and characterised with DLS. Out of the different ratio of samples, a stable ratio has been selected and used for the study. The detail of the optimization ratio is given in the below table:

| Serial No. | Cholesterol-Coconut Oil-Castor Oil ratio | Cholesterol (mg) | Coconut oil (μl) | Castor Oil (μl) | Tween 80 (%) | Total volume of water |
|---|---|---|---|---|---|---|
| 1 | 1:1 | 10 | 5.5 | 5.2 | 1 | 10 |
| 2 | 1:2 | 10 | 11 | 10.4 | 1 | 10 |
| 3 | 1:3 | 10 | 16.5 | 15.6 | 1 | 10 |
| 4 | 1:4 | 10 | 22 | 20.8 | 1 | 10 |
| 5 | 1:5 | 10 | 27.5 | 26 | 1 | 10 |

Cholesterol-Coconut Oil-Castor Oil Nanostructured Lipid Carrier (CHCACO-NLCs) Preparation Method:

Cholesterol-Coconut Oil-Castor Oil of different ratios are taken in a beaker 1 to this added acetone and ethanol in equal ratio. In a beaker 2, 1% tween 80 prepared in aqueous medium is taken. Both the beakers were stirred and heated in a water bath at equal temperature (60-65° C.) for mixing and dissolving the component. After a few minutes, when beaker 1 solvent is almost evaporated, hot 1% tween 80 is added to it, which results in white emulsion formation. The emulsion is stirred at the same temperature for another 5 mins. After 5 mins the emulsion is ultrasonicated for 4 mins at the amplitude of 40%. Further the ultrasonicaticated sample is stirred at RT and high RPM for 1 hr, which results in the formation of the Cholesterol-Coconut Oil-Castor Oil nanostructured lipid carrier (CHCACO-NLCs).

Cholesterol-Coconut Oil-Castor Oil Nanostructured Lipid Carrier (CHCAO-NLCs) Preparation Method (PILOT-SCALE):

Cholesterol-Coconut Oil-Castor Oil of 1:1 ratio is taken in a beaker 1 to this was added acetone and ethanol in equal ratio. In a beaker 2, 1% tween 80 was prepared in aqueous medium. Both the beakers were stirred and heated in a water bath at equal temperature (60-65° C.) for mixing and dissolving the component. After a few minutes, when beaker 1 solvent is almost evaporated, hot 1% tween 80 is added to it, which results in white emulsion formation. The emulsion is stirred at the same temperature for another 5 mins. After 5 mins, emulsion is passed through High Pressure Homogenizer for 5 mins, which results in the formation of the Cholesterol-Castor Oil nanostructured lipid carrier (CHCAO-NLCs).

Characterisation of Lab Scale Sample

Particle size measurement and zeta potential measurement: The particle size and zeta potential of the synthesised sample is characterised by DLS. The characterisation showed that sample with Cholesterol-Coconut Oil-Castor Oil nanostructured lipid carrier (CHCACO-NLCs) ratio 1:1 is the most stable compared to other ratios. The size and zeta potential of CHCACO-NLCs is given in Table 6.

| Sample | Dexamethasone (mg/ml) | Particle size (nm) | Zeta potential (mV) |
|---|---|---|---|
| CHCACO | 0 | 319 | −13.8 |

CHCACO-NLCs is characterised by DLS. It has been observed that CHCACO-NLCs have particle size of 319 nm and zeta potential of −13.8 mV.

Preparation and Characterisation of Dexamethasone Loaded Cholesterol-Coconut Oil-Castor Oil Nanostructured Lipid Carrier (CHCACO-NLCs).

Cholesterol-Coconut Oil-Castor Oil nanostructured lipid carrier of ratios 1:1, dexamethasone 1 mg/ml (0.1% w/v) is taken in a beaker 1 to this added acetone and ethanol in equal ratio. In a beaker 2, 1% tween 80 prepared in aqueous medium is taken. Both the beakers are stirred and heated in a water bath at equal temperature (60-65° C.) for mixing and dissolving the component. After a few minutes, when beaker 1 solvent is almost evaporated, hot 1% tween 80 is added to it, which results in white emulsion formation. The emulsion is stirred at the same temperature for another 5 mins. After 5 mins the emulsion is ultrasonicated for 4 mins at the amplitude of 40%. Further the ultrasonicaticated sample is stirred at room temperature and high RPM for 1 h, which results in the formation of the CHCACO-D-NLCs and characterised by DLS. The size and zeta potential of CHCACO-D-NLCs is given in Table 7.

| Sample | Dexamethasone (mg/ml) | Particle size (nm) | Zeta potential (mV) |
|---|---|---|---|
| CHCACO-D | 1 | 294.4 | −10.2 |

CHCACO-D-NLCs is characterised by DLS. It has been observed that CHCACO-D-NLCs has particle size of 294.4 nm and zeta potential of −10.2 nm.

Encapsulation Efficiency of Dexamethasone Loaded CHLF-D-NLCs

Entrapment efficiency of dexamethasone entrapped in CHCACO-NLCs is determined by HPLC. For this 1 μl of CHCACO-D-NLCs is added to the 999 μl of mobile phase—Phosphate Buffer (pH=3) and acetonitrile (ACN) in ratio 50:50. From the obtained area, the unknown concentration of the drug is determined by calibration curve and entrapment efficiency is calculated by the given formula $$\text{Encapsulation Efficiency (\%)} = \frac{(\text{Drug Loaded} - \text{free unencapsualted drug})}{\text{Drug Loaded}} * 100$$

It has been observed that the encapsulation efficiency (%) of CHCACO-D-NLCs is 97.3%

Experimental Study Performed with CHCACO-NLCs a) Cytotoxicity Assessment of the Prepared CHCACO-NLC The cytotoxicity of the CHCACO-NLCs was carried out on Human Corneal Epithelium Cell (HCEC). The cells with the initial density of 10,000 cells/well were seeded in a 96-well plate and were then cultured for 24 h in DMEM medium containing 10% FBS. The cells were then treated with varying concentrations of CHCACO-NLCs, and CHCACO-D-NLCs treated cells were incubated in a humidified environment with 5% $CO_2$ at 37° C. for 4 h. After 4 h culture medium is replaced with the fresh medium, the cells were further maintained for another 20 hours. After the specified time, MTT reagent was added to each well, and the cells were incubated for another 4 hours. The medium in each well was replaced with 200 μl of DMSO to dissolve the formazan crystals. The absorbance (O.D.) was recorded with a microplate reader. The cell viability was calculated by using the following equation:

$$\text{Cell viability (\%)} = \left[\frac{O.D.\text{ (test)}}{O.D.\text{ (control)}}\right] * 100$$

Where O.D. (test) and O.D. (control) are the absorbance values of the cells cultured with and without NLC, respectively. The cytotoxicity study showed that prepared 1:1 ratio CHCACO-NLCs is non-toxic up to the given concentration FIG. 31,32.

b) Cellular Uptake Study

In vitro cellular uptake of coumarin-6 labelled CHCACO-NLCs was further examined using fluorescent microscopy. The cells were seeded in confocal imaging dishes at a density of $5\times10^4$ cells per dish. The coumarin-6 labelled CHCACO-NLCs were prepared and were exposed to the HCEC cells medium. After 4 hours of incubation at 37° C., CHCACO-NLCs treated medium is removed and cells are washed. A further cellular uptake study was performed under fluorescent microscope. The data showed that NLCs are internalised in the cells and the coumarin-6, which is encapsulated in CHCACO-NLCs is successfully released in the cytoplasm of the HCEC cells. Indicating that dexamethasone encapsulated in CHCACO-NLCs will be released within the HCEC cells (FIG. 33).

c) Mucoadhesion Study

A mucoadhesion study was performed ex vivo with pig cornea. The mucoadhesion study of coumarin-6 labelled CHCACO-NLCs on pig cornea was further examined using fluorescent microscopy. The pig cornea is excised and placed in the confocal imaging dishes containing medium. The coumarin-6 labelled CHCACO-NLCs were prepared and were exposed to the cornea in medium. After 4 hours of incubation at 37° C., CHCACO-NLCs treated medium is removed and the cornea is washed. A further mucoadhesion study was performed under fluorescent microscope. The mucoadhesion study showed that the CHCACO-NLCs are mucoadhesive. As the CHLF-NLCs particles stick to the cornea (FIG. 34).

d) Drug Release Study

A drug release study was performed with drug encapsulated CHCACO-NLCs with the drug concentration 1 mg/ml over the time of 93.5 hours. The drug release study is performed by dialysis membrane. 1 ml of the drug loaded CHCACO-NLCs is taken in the dialysis membrane with concentration of drug 1 mg/ml. The membrane is clipped and dipped into the phosphate buffer saline (PBS) of pH=7.4 and temperature is maintained 37° C. The PBS is stirred with magnetic bead. The 1 ml of the PBS is collected after different time interval and 1 ml of fresh PBS is added to maintain the volume of the PBS. The collected sample is analysed with the HPLC. The drug release data showed that drug is released over the time of 93.5 hours (FIG. 35).

e) Permeation Study

The permeation study was performed ex vivo with pig cornea. The excised cornea fit in the Franz diffusion cell. The donor chamber is filled with drug loaded CHCACO-NLCs (concentration of drug 1 mg/ml). In the acceptor chamber PBS of pH=7.4 is taken and stirred with magnetic bead and the chamber is maintained at the temperature of 37° C. The 1 ml of the PBS is collected after different time interval and 1 ml of fresh PBS is added to maintain the volume of the PBS in acceptor chamber. The collected sample is analysed with the HPLC. For the reference marketed formulation Maxidex is used for permeation. The study showed that dexamethasone is efficiently permeated through the cornea (FIG. 36).

The invention claimed is:

1. A Nanostructured Lipid Carrier (NLC) particle comprising a therapeutic agent encapsulated therein for ocular delivery of the therapeutic agent, wherein the NLC comprises:
- (i) a solid outer shell comprising a solid lipid, and
- (ii) a liquid core comprising a liquid lipid, wherein the liquid lipid comprises a medium chain triglyceride (MCT) and/or castor oil, or a castor oil component selected from the group consisting of ricinoleic acid (C18), linoleic acid (C18), oleic acid (C18), stearic acid (C18), palmitic acid (C16), dihydroxystearic acid (C18), and linolenic acid (C18);
- wherein the core comprises the therapeutic agent; and
- wherein the ratio of solid lipid to liquid lipid is 1:30 to 1:4 (w/v), and
- wherein the NLC particle provides sustained release of the therapeutic agent for at least 48 hours.

2. The NLC particle according to claim 1, wherein the solid lipid of the solid outer shell comprises a solid lipid selected from the group consisting of tristearin, stearic acid, cetyl palmitate, cholesterol, glyceryl distearate NF/glyceryl palmitostearate, esters of behenic acid with glycerol, tripalmitin, tristearin, hydrogenated palm oil, cetyl palmitate, glyceryl stearate, glycerol monostearate, glycerol monostearate and PEG-75 stearate (e.g. Gelot® 64), cetyl alcohol and ceteth-20/steareth-20, cholesterol and combinations thereof.

3. The NLC particle according to claim 1, wherein the solid lipid of the solid outer shell consists of cholesterol.

4. The NLC particle according to claim 1,
- wherein the liquid lipid of the liquid core comprises a lipid selected from the group consisting of paraffin oil, 2-octyl dodecanol, oleic acid, squalene, isopropyl myristate, vitamin E, triglycerides of the fractionated plant fatty acids C8 and C10, diethylene glycol monoethyl ether NF, medium-chain triglycerides of caprylic (C8) and capric (C10) acids, propylene glycol dicaprylocaprate, propylene glycol monolaurate, propylene glycol monocaprylate, and combinations thereof; or
- wherein the liquid lipid of the liquid core comprises coconut oil, or an equivalent, fraction or component thereof, and castor oil, or an equivalent, fraction or component thereof; or
- wherein the liquid lipid of the liquid core comprises medium-chain triglycerides of caprylic (C8) and capric (C10) acids.

5. The NLC particle according to claim 1, wherein the medium chain triglyceride comprises:
- triglycerides of fatty acids selected from the group consisting of caproic acid, enanthic acid, caprylic acid, nonanoic acid, capric acid, lauric acid, and combinations thereof; or
- triglycerides of capric acid (C10) and/or caprylic acid (C8).

6. The NLC particle according to claim 1, wherein the therapeutic agent is suitable for treatment or prevention of an eye disorder.

7. The NLC particle according to claim 6, wherein the eye disorder comprises any one of the disorders selected from dry eye syndrome (keratoconjunctivitis sicca); conjunctivitis; keratitis; uveitis; scleritis; episcleritis; blepharitis; *acanthamoeba keratitis*; iritis; or combinations thereof.

8. The NLC particle according to claim 1, wherein the therapeutic agent is hydrophobic.

9. The NLC particle according to claim 1, wherein the therapeutic agent is an anti-inflammatory agent.

10. The NLC particle according to claim 9, wherein the anti-inflammatory agent comprises or consists of a corticosteroid.

11. The NLC particle according to claim 10, wherein the corticosteroid may be selected from the group consisting of fluocinolone, difluprednate, loteprednol, fluorometholone, medrysone, dexamethasone, prednisolone, triamcinolone, rimexolone, and combinations thereof.

12. The NLC particle according to claim 1, wherein the therapeutic agent comprises an antihistamine and/or decongestant.

13. The NLC particle according to claim 1, wherein the therapeutic agent is provided at a concentration of between about 0.01 mg/ml and about 1 mg/ml.

14. The NLC particle according to claim 1, wherein the therapeutic agent is provided in combination with one or more other therapeutically active agents.

15. The NLC particle according to claim 1, wherein the NLC particle is nanoparticle size.

16. A composition comprising a plurality of NLC particles comprising a therapeutic agent encapsulated therein in accordance with claim 1.

17. The composition according to claim 16, wherein the composition is an ophthalmically acceptable composition.

18. A method of treatment or prevention of an eye disorder in a subject comprising the administration of the NLC particle according to claim 1 to an eye of the subject.

19. The method according to claim 18, wherein the administration is topical to the surface of the eye or to the eyelid.

* * * * *